(12) United States Patent (10) Patent No.: US 7,393,342 B2
Henniges et al. (45) Date of Patent: Jul. 1, 2008

(54) BONE CEMENT MIXING AND DELIVERY SYSTEM INCLUDING A DELIVERY GUN AND A CARTRIDGE HAVING A PISTON, THE DELIVERY GUN CONFIGURED TO RELEASE THE PISTON

(75) Inventors: Bruce D. Henniges, Galesburg, MI (US); Jared P. Coffeen, Paw Paw, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 11/837,649

(22) Filed: Aug. 13, 2007

(65) Prior Publication Data
US 2008/0025140 A1 Jan. 31, 2008

Related U.S. Application Data

(62) Division of application No. 10/843,813, filed on May 12, 2004.
(60) Provisional application No. 60/520,877, filed on Nov. 18, 2003, provisional application No. 60/469,651, filed on May 12, 2003.

(51) Int. Cl.
*A61M 5/00* (2006.01)
*G01F 11/32* (2006.01)
*B01F 15/02* (2006.01)

(52) U.S. Cl. ......................... 604/187; 366/189; 222/327
(58) Field of Classification Search ................. 366/189, 366/184; 222/327, 326, 325; 604/187, 181
See application file for complete search history.

(56) References Cited
U.S. PATENT DOCUMENTS
949,163 A 2/1910 Stapley

| | | |
|---|---|---|
| 1,211,426 A | 1/1917 | Farrington |
| 1,612,996 A | 1/1927 | Waagbo |
| 1,694,845 A | 12/1928 | De Trey |
| 2,745,575 A | 5/1956 | Spencer |

(Continued)

FOREIGN PATENT DOCUMENTS

| | | |
|---|---|---|
| DE | 3708442 A1 | 9/1988 |
| DE | 4022985 C2 | 1/1992 |
| DE | 4030823 A1 | 4/1992 |
| DE | 4243877 A1 | 7/1994 |
| EP | 0380876 B1 | 2/1996 |

(Continued)

OTHER PUBLICATIONS

Office Action from U.S. Appl. No. 10/843,813, filed May 12, 2004.

(Continued)

*Primary Examiner*—Tony G Soohoo
(74) *Attorney, Agent, or Firm*—Howard & Howard Attorneys, P.C.

(57) ABSTRACT

A bone cement mixing and delivery system is provided. The system includes a mixing cartridge for receiving liquid and powder components of bone cement, a mixing device for mixing the components, and a delivery gun for discharging the bone cement from the mixing cartridge. The mixing cartridge comprises a cylinder having proximal and distal ends with a cylinder wall extending between the ends. A piston is locked at the distal end by a locking member that includes a pair of locking tabs protruding into slots in the cylinder wall. With the piston in the locked position, the mixing device, e.g., a mixing shaft and blade, mixes the components. After mixing, the cartridge is placed in the delivery gun and release buttons on the locking member are engaged by a release mechanism on the delivery gun to release the piston from the locked position.

12 Claims, 22 Drawing Sheets

U.S. PATENT DOCUMENTS

| | | |
|---|---|---|
| 2,874,877 A | 2/1959 | Spencer |
| 3,036,819 A | 5/1962 | Peterson |
| 3,140,078 A | 7/1964 | Krahe et al. |
| 3,144,966 A | 8/1964 | Cook |
| 3,216,616 A | 11/1965 | Blankenship, Jr. |
| 3,217,946 A | 11/1965 | Cook |
| 3,459,341 A | 8/1969 | Copeland |
| 3,815,790 A | 6/1974 | Allen et al. |
| 3,873,008 A | 3/1975 | Jahn |
| 4,189,665 A | 2/1980 | van der Meulen |
| 4,269,331 A | 5/1981 | Watson |
| 4,277,184 A | 7/1981 | Solomon |
| 4,338,925 A | 7/1982 | Miller |
| 4,371,094 A | 2/1983 | Hutter, III |
| 4,405,249 A | 9/1983 | Scales |
| 4,461,407 A | 7/1984 | Finnegan |
| 4,463,875 A | 8/1984 | Tepic |
| 4,546,767 A | 10/1985 | Smith |
| 4,583,974 A | 4/1986 | Kokernak |
| 4,653,487 A | 3/1987 | Maale |
| 4,671,263 A | 6/1987 | Draenert |
| 4,676,406 A | 6/1987 | Frischmann et al. |
| 4,676,655 A | 6/1987 | Handler |
| 4,693,656 A | 9/1987 | Guthrie |
| 4,721,390 A | 1/1988 | Lidgren |
| 4,758,096 A | 7/1988 | Gunnarsson |
| 4,832,692 A | 5/1989 | Box et al. |
| 4,966,601 A | 10/1990 | Draenert |
| 4,994,065 A | 2/1991 | Gibbs et al. |
| 5,071,040 A | 12/1991 | Laptewicz, Jr. |
| 5,100,241 A | 3/1992 | Chan |
| 5,181,636 A | 1/1993 | Anderson et al. |
| 5,193,907 A | 3/1993 | Faccioli et al. |
| 5,252,301 A | 10/1993 | Nilson et al. |
| 5,306,248 A | 4/1994 | Barrington |
| 5,308,340 A | 5/1994 | Harris |
| 5,328,262 A | 7/1994 | Lidgren et al. |
| 5,341,964 A | 8/1994 | Medved |
| 5,370,221 A | 12/1994 | Magnusson et al. |
| 5,431,654 A | 7/1995 | Nic |
| 5,501,374 A | 3/1996 | Laufer et al. |
| 5,501,520 A | 3/1996 | Lidgren et al. |
| 5,514,135 A | 5/1996 | Earle |
| 5,549,380 A | 8/1996 | Lidgren et al. |
| 5,549,381 A | 8/1996 | Hays et al. |
| 5,551,778 A | 9/1996 | Hauke et al. |
| 5,556,009 A | 9/1996 | Motzko |
| 5,588,745 A | 12/1996 | Tanaka et al. |
| 5,624,184 A | 4/1997 | Chan |
| 5,638,997 A | 6/1997 | Hawkins et al. |
| 5,681,317 A | 10/1997 | Caldarise |
| 5,762,237 A | 6/1998 | Chang |
| 5,779,356 A | 7/1998 | Chan |
| 5,797,678 A | 8/1998 | Murray |
| 5,829,875 A | 11/1998 | Hagel et al. |
| 5,842,785 A | 12/1998 | Brown et al. |
| 5,842,786 A | 12/1998 | Solomon |
| 5,876,116 A | 3/1999 | Barker et al. |
| 5,893,488 A | 4/1999 | Hoag et al. |
| 5,934,803 A | 8/1999 | Hutter |
| 6,017,349 A | 1/2000 | Heller et al. |
| 6,019,765 A | 2/2000 | Thornhill et al. |
| 6,042,262 A | 3/2000 | Hajianpour |
| 6,045,555 A | 4/2000 | Smith et al. |
| 6,048,346 A | 4/2000 | Reiley et al. |
| 6,083,229 A | 7/2000 | Constantz et al. |
| 6,086,594 A | 7/2000 | Brown |
| 6,120,174 A | 9/2000 | Hoag et al. |
| 6,149,655 A | 11/2000 | Constantz et al. |
| 6,155,463 A | 12/2000 | Dentler |
| 6,176,607 B1 | 1/2001 | Hajianpour |
| 6,260,737 B1 | 7/2001 | Gruendeman |
| 6,296,149 B1 | 10/2001 | Long |
| 6,312,149 B1 | 11/2001 | Sjovall et al. |
| 6,367,962 B1 | 4/2002 | Mizutani et al. |
| 6,406,175 B1 | 6/2002 | Marino |
| 6,547,432 B2 | 4/2003 | Coffeen et al. |
| 6,550,957 B2 | 4/2003 | Mizutani et al. |
| 6,592,247 B1 | 7/2003 | Brown et al. |
| 6,599,293 B2 | 7/2003 | Tague et al. |
| 6,736,537 B2 | 5/2004 | Coffeen et al. |
| 6,755,563 B2 | 6/2004 | Wahlig et al. |
| 2002/0191484 A1 | 12/2002 | Jonsson |
| 2002/0191485 A1 | 12/2002 | Jonsson |
| 2003/0086332 A1 | 5/2003 | Jonsson |

FOREIGN PATENT DOCUMENTS

| | | |
|---|---|---|
| EP | 0528447 B1 | 1/1997 |
| WO | WO 03/084445 | 10/1903 |
| WO | WO 87/05492 | 9/1987 |
| WO | WO 90/13264 | 11/1990 |
| WO | WO 93/22041 | 11/1993 |
| WO | WO 95/00240 | 1/1995 |
| WO | WO 97/18031 | 5/1997 |
| WO | WO 97/21485 | 6/1997 |
| WO | WO 99/67015 | 12/1999 |

OTHER PUBLICATIONS

Search Report, Application No. PCT/US04/14749, filing date May 12, 2004.

Office Action Fron U.S. Appl. No. 10/991,894, filed Nov. 18, 2004.

"Vacu-Mix Plus—Cementing the Future"; DePuy CMW; DePuy Int'l Ltd., St. Anthony's Road, Leeds LSII 8DT England; 4 page product brochure, no date.

"MixOR System"; Smith & Nephew; Smith & Nephew, Inc., 1450 Brooks Road, Memphis, TN 38116; 9 page product brochure, no date.

"Generation 4 Bone Cement—In the VacPac Mixing and Delivery System—Designed for the Surgical Staff"; Biomet Orthopedics, inc.; PO Box 587, Warsaw, IN 46581; no date.

www.biomet.com; 6 page Technical Brochure, no date.

"Cemvac Ultra—Pre-Loaded Cement Syringe System"; De-Puy Int'l Ltd., St. Anthony's Road, Leeds LSI1 8DT England; 4 page product brochure, no date.

"Advantages of the Optivac Mixing System"; US Patent No. 4,721,390,5,328,262 and 5,501,620; Wang J. S. et al.; J. Biomet Mailer Res (Appl. Bomator) 1996; 33. 115-119.

"Quick-Vac Vacuum Mixing System"; Zimmer; 1 page product brochure, no date.

"The Scan Optivac—Part of the Scan Cementation System" Part of the Scan Cementation System; ScandiMed AG, Forskagegatan 1, S-275 37 Sjobo, Sweden; www.scandimed.com;1 page product brochure, no date.

"TwistOR—Vacuum Bone Cement Mixing/Dispensing System"; Immedica, 100 Passaic Ave., Chatham NJ 07298; www.immedica. com; 1 page product brochure, no date.

"Effect of Mixing Technique on the Properties of Acrylic Bone-Cement—A Comparison of Syringe and Bowl Mixing Systems"; J. M. Wilkinson, FRCS, R. Eveleigh, PhD., no date.

A. J. Hamer, FRCS (Orth), A. Milne, DCR, A.W. Miles, MSc (Eng.), and I. Stockley, FRCS; The Journal of Antorplasty vol. 15, No. 5 Aug. 2000; pp. 663-666.

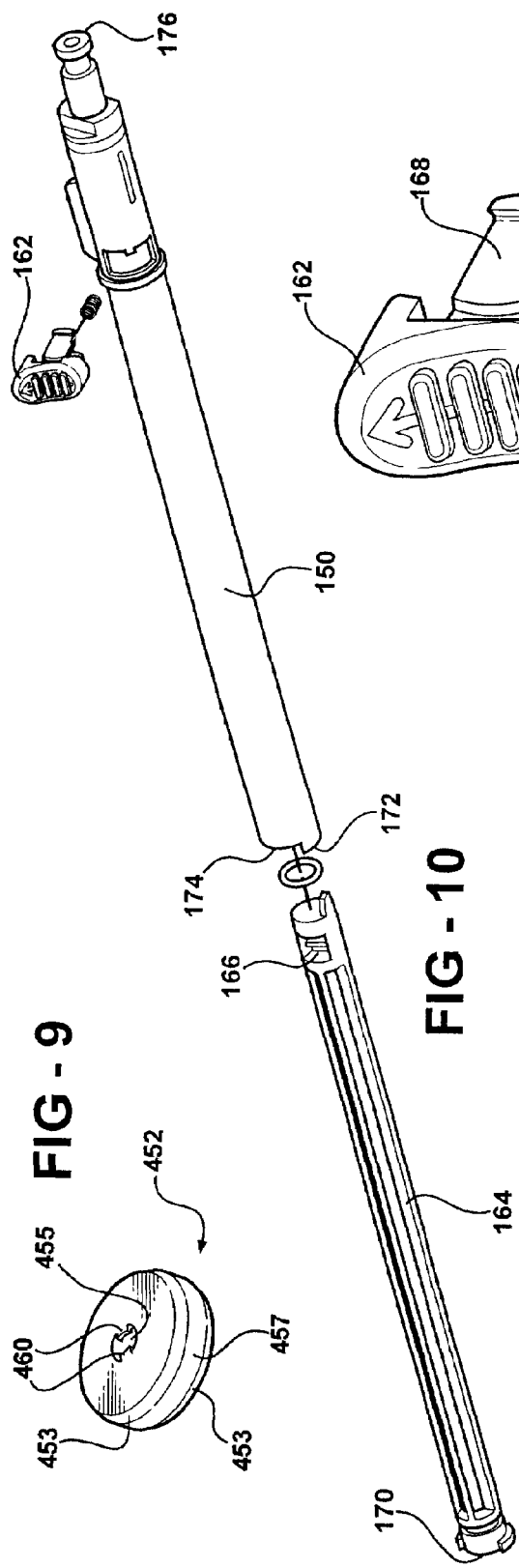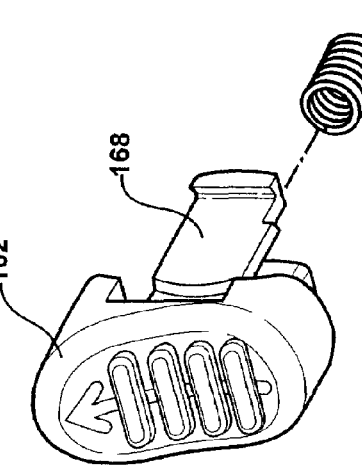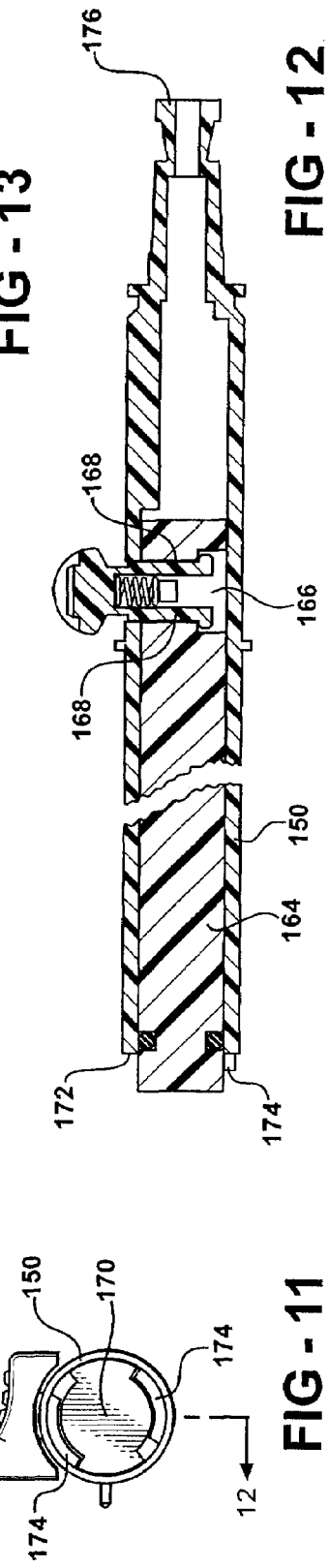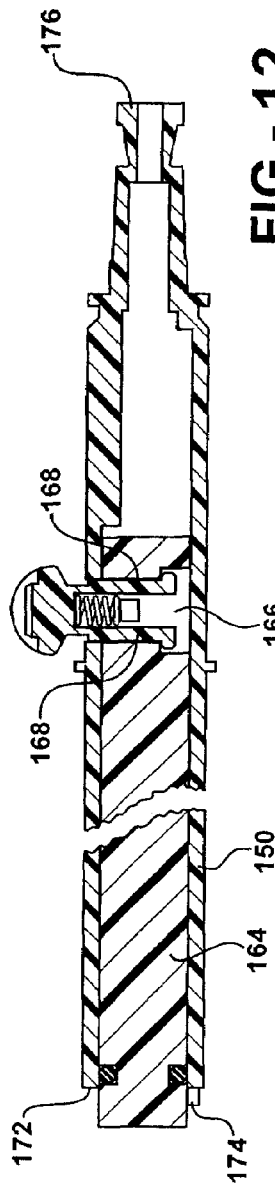

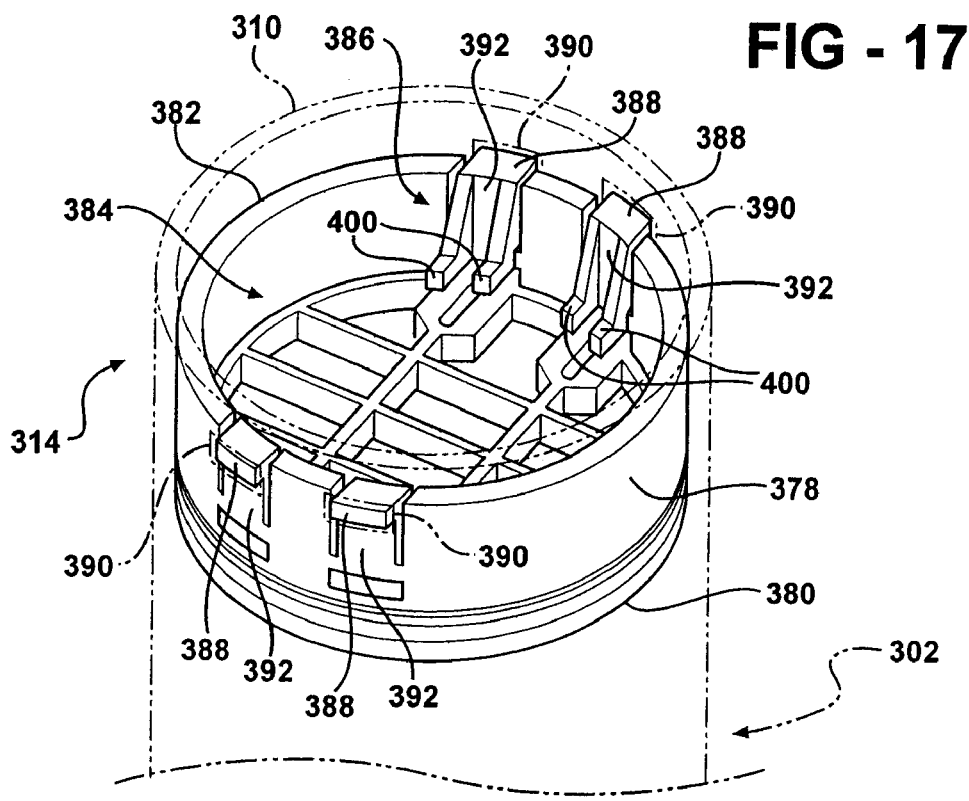
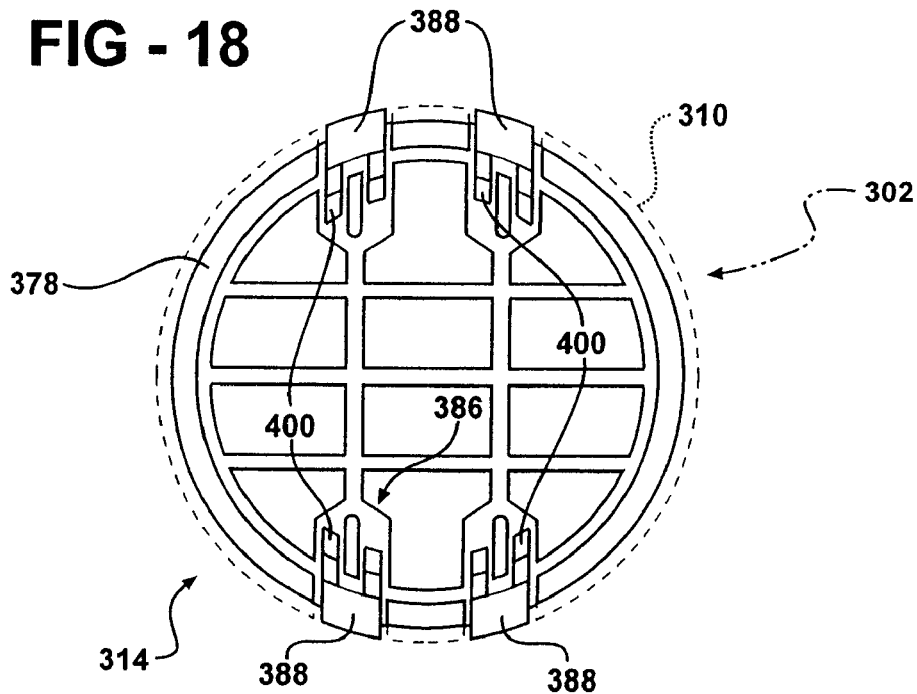

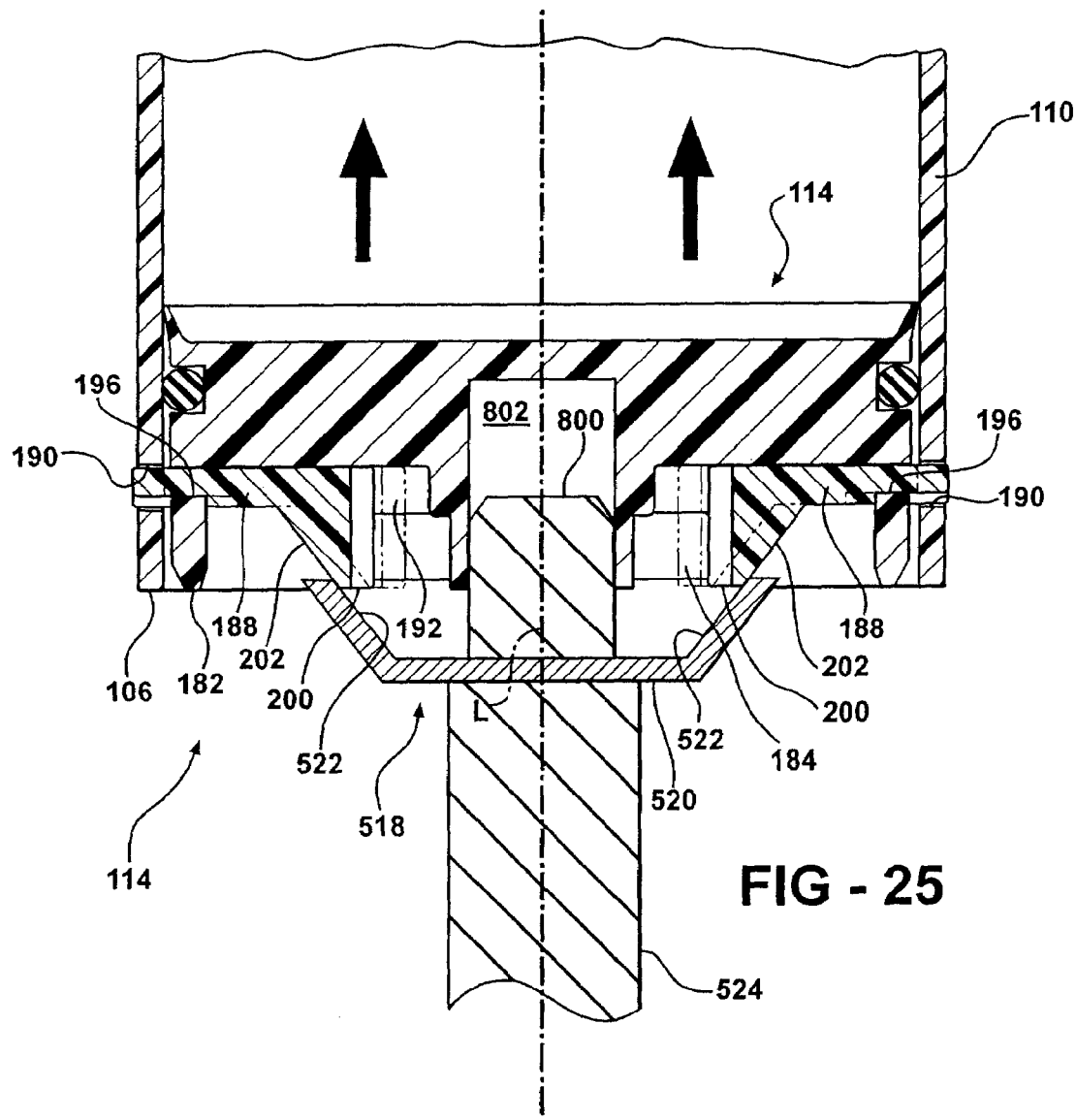

BONE CEMENT MIXING AND DELIVERY SYSTEM INCLUDING A DELIVERY GUN AND A CARTRIDGE HAVING A PISTON, THE DELIVERY GUN CONFIGURED TO RELEASE THE PISTON

RELATED APPLICATIONS

This application is a divisional of application Ser. No. 10/843,813, filed May 12, 2004, and claims the benefit of U.S. Provisional Patent Application Ser. No. 60/469,651, filed May 12, 2003 and U.S. Provisional Patent Application Ser. No. 60/520,877, filed Nov. 18, 2003. The advantages and disclosures of each of the aforementioned applications are hereby incorporated by reference.

FIELD OF THE INVENTION

The present invention generally relates to a bone cement mixing and delivery system. More specifically, the present invention relates to a mixing cartridge for receiving liquid and powder components of bone cement to be mixed, a mixing device for mixing the components, and a delivery gun for discharging the bone cement from the mixing cartridge into an anatomical site of a patient.

BACKGROUND OF THE INVENTION

Bone cement mixing and delivery systems are well known for mixing liquid and powder components of bone cement and delivering the prepared bone cement to an anatomical site during various surgical procedures. Bone cement is particularly useful in orthopedic procedures in which a prosthetic device is fixed to a bone or joint structure to improve the strength, rigidity, and movement of the structure. In a total hip arthroplasty (THA) procedure, in which a hip joint is replaced with a prosthetic device, bone cement is used to fix the prosthetic device in place in a medullary canal of a femur.

Typically, the bone cement is prepared in a mixing cartridge. The mixing cartridge includes a cylinder having proximal and distal ends with a mixing chamber defined between the ends. The mixing cartridge further includes a cap covering the proximal end of the cylinder and a piston disposed in the distal end of the cylinder such that the mixing chamber is further defined between the cap and the piston. The piston may be releasably secured in a locked position in the cylinder by a cotter pin. The cap supports a mixing device, i.e., a mixing shaft and blade, for mixing the liquid and powder components of the bone cement in the mixing chamber.

Once the bone cement is mixed, the mixing cartridge is prepared for inserting into a delivery gun to discharge the bone cement. This may include disengaging the mixing shaft and coupling a nozzle to the cap to provide a discharge point for the bone cement. At the same time, the piston is released from the locked position in the distal end of the cylinder by pulling the cotter pin. This allows the piston to be driven by the delivery gun through the mixing chamber to discharge the bone cement from the nozzle. An alternative solution for securing and releasing the piston is shown in U.S. Pat. No. 5,328,262 to Lidgren et al.

In Lidgren et al., the piston is releasably secured in the locked position in the distal end of the cylinder by a gripping portion in the form of a flange, which extends along only a portion of an inner periphery of the cylinder. The piston in Lidgren et al. has a corresponding gripping portion in the form of an outwardly directed lip that protrudes behind the flange. The lip defines a groove with an outer surface of the piston to receive the flange. To release the piston from the locked position, the flange is rotated through the groove until the flange has been rotated past the lip. Lidgren et al. discloses a base that is used to secure the piston from rotation while a user rotates the cylinder relative to the piston to release the piston from the locked position. This method of releasing the piston from the locked position, much like pulling the cotter pin, requires additional manipulation by a user.

Once the piston is released from the locked position, the mixing cartridge is inserted into the delivery gun. A typical delivery gun includes a ram disk that engages the piston and drives the piston through the mixing chamber to discharge the bone cement from the nozzle. The delivery gun includes a cradle for supporting the mixing cartridge and a casing for supporting a drive rod that engages the ram disk and advances the ram disk to drive the piston. The drive rod includes a plurality of teeth and a pawl member engages the teeth to advance the drive rod. A trigger supports the pawl member and the casing rotatably supports the trigger. Actuation of the trigger relative to the casing urges the pawl member against the teeth to advance the drive rod.

An example of such a delivery gun is illustrated in U.S. Pat. No. 5,431,654 to Nic. In the '654 patent to Nic, two pawl members are used to independently advance the drive rod and the ram disk. The pawl members provide high speed/low force and low speed/high force advancement of the drive rod. A switch is used to select between the speeds. When high speed is selected, both pawl members engage the drive rod, while only the high-speed pawl member actually advances the drive rod. When low speed is selected, the high-speed pawl member is isolated from the teeth such that only the low speed pawl member engages the teeth to advance the drive rod. However, in Nic, the trigger directly supports each of the pawl members which results in a low mechanical advantage to advance the drive rod and ram disk.

BRIEF SUMMARY OF THE INVENTION

A mixing cartridge for receiving liquid and powder components of bone cement to be mixed for medical use. The mixing cartridge comprises a cylinder having proximal and distal ends with a mixing chamber defined therebetween. The cylinder includes a cylinder wall extending between the ends about a longitudinal axis of the cylinder. A piston is disposed in the cylinder at the distal end such that the mixing chamber is further defined between the proximal end and the piston. A locking member is coupled to the piston to lock the piston in the distal end. The locking member includes a male portion engaging a female portion in the cylinder wall to place the piston in a locked position at the distal end of the cylinder. The locking member includes a resilient portion for biasing the male portion into mating engagement with the female portion. The piston remains in the locked position at the distal end of the cylinder while mixing the liquid and powder components.

One advantage of the mixing cartridge is the conveniently positioned locking member used to lock the piston in the distal end. By using the resilient portion to bias the male portion into mating engagement with the female portion, a user can easily release the piston from the locked position by either manually or mechanically acting against the bias of the resilient portion to disengage the male and female portions.

A delivery gun is also provided for discharging the bone cement from the cartridge once the bone cement is prepared. The delivery gun comprises a casing for supporting the cartridge. A drive mechanism is supported by the casing and advanceable relative to the casing to force the bone cement from the cartridge. The casing pivotally supports a trigger operatively connected to the drive mechanism to advance the drive mechanism upon actuation of the trigger to force the bone cement from the cartridge. A linkage system works in conjunction with the trigger to advance the drive mechanism. The linkage system comprises a first link pivotally connected to the casing and a second link interconnecting the first link and the trigger such that actuating the trigger moves the second link and the first link to advance the drive mechanism.

An advantage of the delivery gun is the use of the linkage system to increase the mechanical advantage needed to successfully advance the drive mechanism and force the bone cement from the cartridge while minimizing fatigue to a user of the delivery gun.

In one aspect of the delivery gun, the drive mechanism includes a drive rod and gripper plates to advance the drive rod. The gripper plates frictionally engage the drive rod to advance the drive rod when the trigger is actuated. In one embodiment, the gripper plates include mating pegs and notches to align adjacent gripper plates. In another embodiment, the gripper plates are coated to increase lubricity and corrosion resistance thereof.

In another aspect of the delivery gun, the drive mechanism includes a drive rod and first and second pawl members to advance the drive rod. In one embodiment, the second pawl member is movable into engagement with teeth on the drive rod for high-speed advancement of the drive rod and out from engagement with the teeth for low-speed advancement. During low-speed advancement, only the first pawl member engages the teeth to advance the drive rod. During high-speed advancement, both pawl members engage the teeth, but only the second pawl member works to advance the drive rod.

A bone cement mixing and delivery system is also provided. The mixing and delivery system includes the cartridge and the delivery gun. In this aspect of the invention, the locking member includes a release button to release the piston from the locked position. At the same time, the delivery gun includes a release mechanism integrated into the drive mechanism to engage the release button. When the cartridge is placed into the cradle of the delivery gun, the drive mechanism is advanced and the release mechanism engages the release button to release the piston from the locked position. This configuration reduces the number of steps typically associated with releasing the piston. By incorporating the release mechanism into the drive mechanism, when the drive mechanism is advanced, the piston is automatically released.

A bone cement loading system for receiving the liquid and powder components of the bone cement is also provided. The loading system includes the cylinder with the piston locked in the distal end. A base defining a cavity is provided for receiving and securing the distal end of the cylinder. A funnel is provided for coupling to the proximal end of the cylinder to channel the powder component of the bone cement into the mixing chamber. The funnel has a proximal end with an oblong oval-shaped periphery to facilitate loading of the powder component of the bone cement into the mixing chamber and a distal end with a circular periphery for snugly fitting into the proximal end of the cylinder. One particular advantage to this loading system is the use of the oblong oval-shaped funnel. The shape of the funnel reduces any mess typically associated with filling the mixing chamber with powder.

A bone cement mixing system comprising the mixing cartridge and a mixing shaft and blade is also provided. The blade is coupled to the mixing shaft and disposed in the mixing chamber for rotating with the mixing shaft about the longitudinal axis to mix the liquid and powder components of the bone cement. The blade includes a center hub coupled to the mixing shaft and an outer ring extending from the center hub. The outer ring forms an acute angle with the longitudinal axis of between twenty and seventy degrees to ensure adequate mixing of the bone cement in the mixing chamber.

A method of mixing the liquid and powder components of the bone cement in the mixing chamber is also provided. The method includes using a rotary power tool connected to a portion of the mixing shaft extending outside of the mixing chamber to mix the liquid and powder components of the bone cement. The blade is disposed in the mixing chamber while being operatively connected to the portion of the mixing shaft extending outside of the mixing chamber. In the method, the rotary power tool is first connected to the portion of the mixing shaft extending outside of the mixing chamber. Then the rotary power tool is actuated to rotate the blade and mix the liquid and powder components of the bone cement. At the same time, the rotary power tool is axially displaced relative to the mixing cartridge to completely mix the liquid and powder components of the bone cement. Once mixing is complete, the operative connection between the blade and the portion of the mixing shaft extending outside of the mixing chamber is removed.

BRIEF DESCRIPTION OF THE SEVERAL VIEWS OF THE DRAWINGS

Advantages of the present invention will be readily appreciated as the same becomes better understood by reference to the following detailed description when considered in connection with the accompanying drawings wherein:

FIGS. 8-8A and 9 are perspective views of alternative blades;

FIG. 10 is a an exploded perspective view of the mixing shaft and a latch rod;

FIG. 11 is an elevational end view of the mixing shaft and latch rod of FIG. 10;

FIG. 12 is a cross-sectional view of the mixing shaft and latch rod of FIGS. 10 and 11;

FIG. 13 is an exploded perspective view of a release latch coupling the mixing shaft and latch rod;

FIG. 17 is a perspective view of an alternative piston of the mixing cartridge;

FIG. 18 is a top view of the alternative piston of FIG. 17;

FIG. 25 is an elevational view illustrating release of a locking member securing the piston;

DETAILED DESCRIPTION OF THE INVENTION

Referring to the Figures, wherein like numerals indicate like or corresponding parts throughout the several views, a bone cement mixing and delivery system is generally shown. The bone cement mixing and delivery system comprises a mixing cartridge 100 for receiving liquid monomer and powdered copolymer components of bone cement to be mixed, a mixing device (mixing shaft 150 and blade 152) for mixing the components, and a delivery device, e.g., a delivery gun 500, for discharging the bone cement from the mixing cartridge 100 into an anatomical site (not shown). An exemplary use for the bone cement is to secure a prosthetic device used to replace a joint structure such as in a total hip arthroplasty (THA) procedure.

Figure 1:
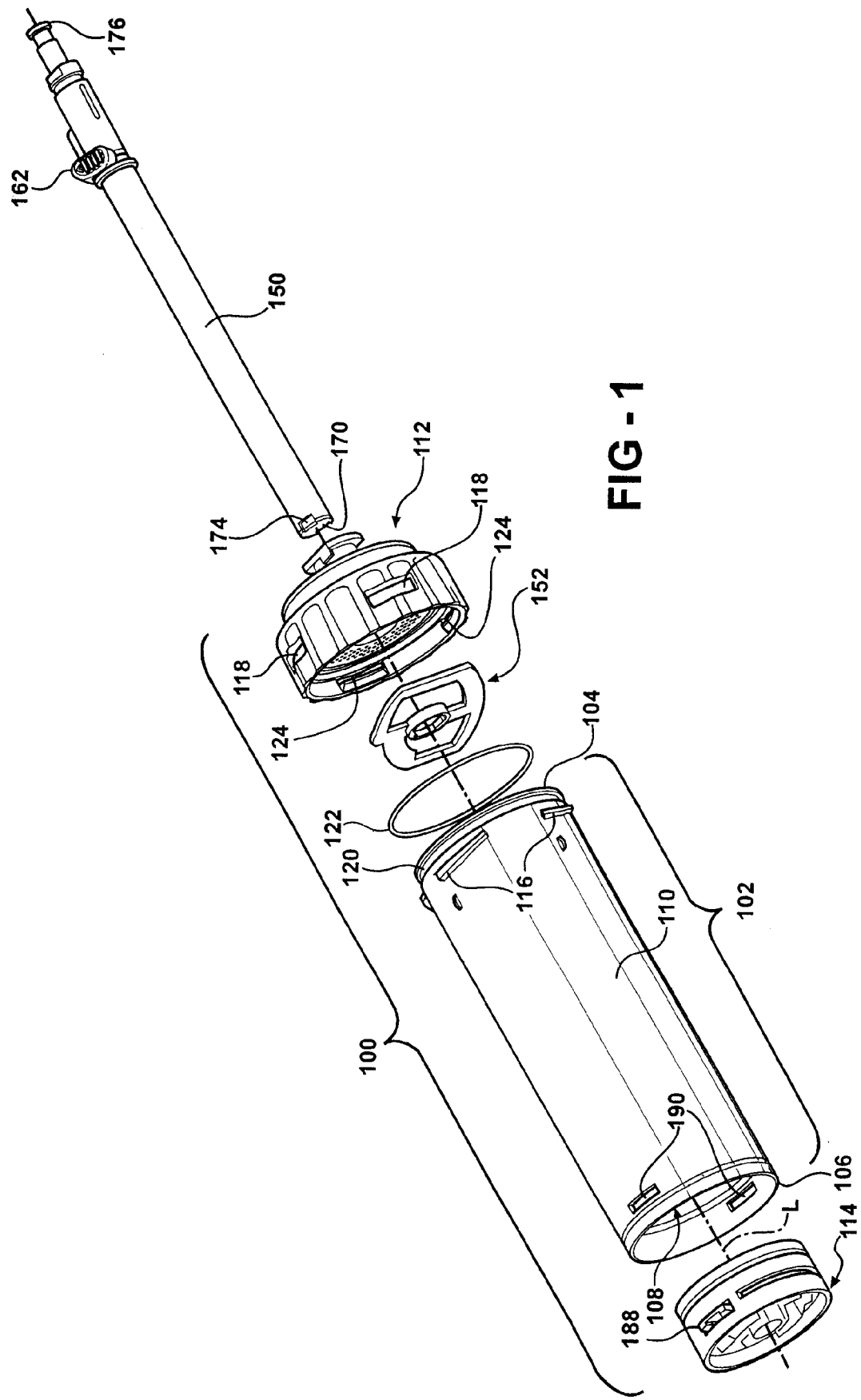
FIG. 1 is an exploded perspective view of a mixing cartridge of the present invention in combination with a mixing shaft and blade.
Figure 2:
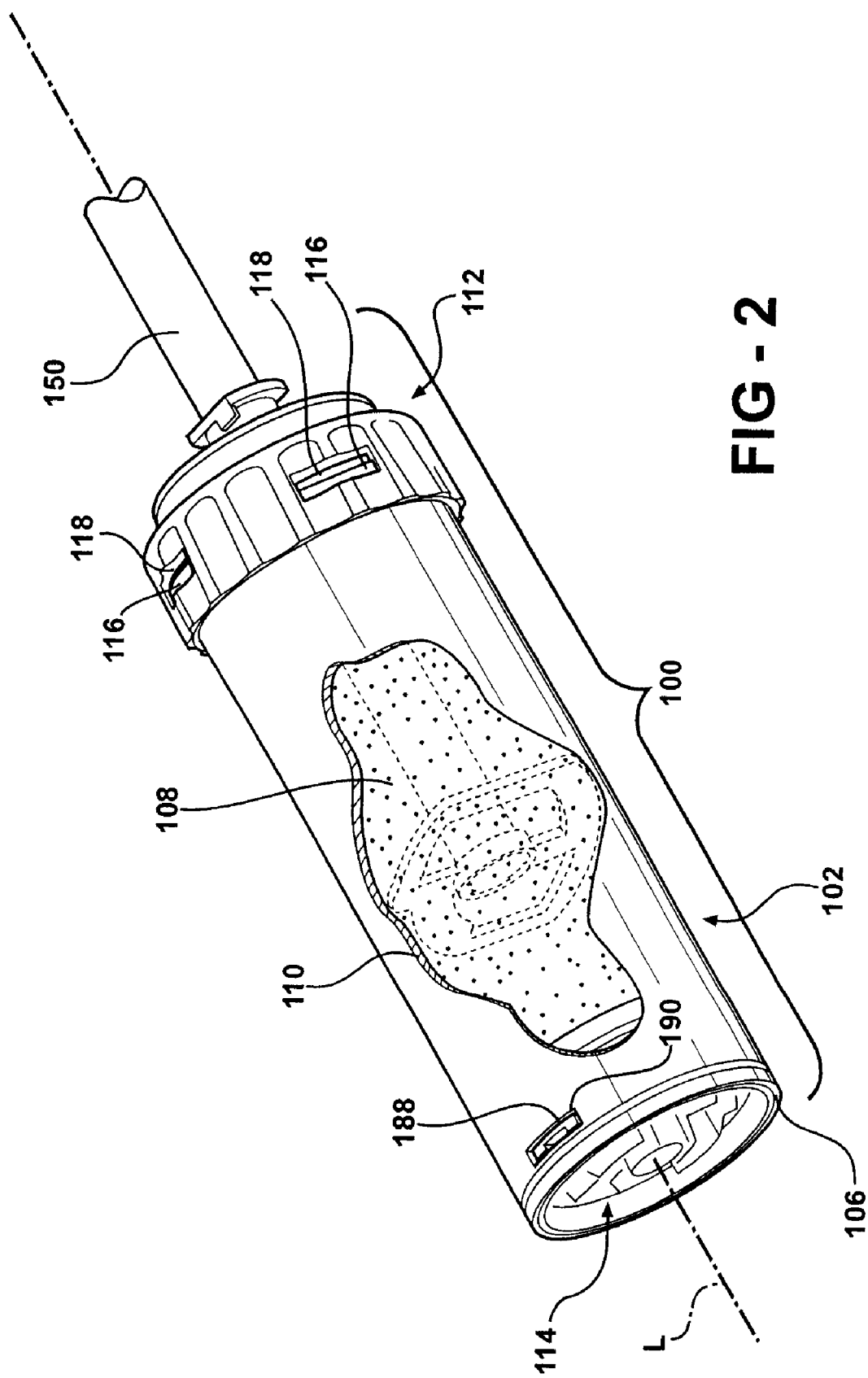
FIG. 2 is an assembled perspective view of the mixing cartridge with the mixing shaft and blade supported therein.

Referring to FIGS. 1 and 2, the bone cement mixing system comprises the mixing cartridge 100 in combination with the mixing shaft 150 and blade 152 used to mix the components of the bone cement in the mixing cartridge 100. The mixing cartridge 100 includes a cylinder 102 having proximal 104 and distal 106 ends. A mixing chamber 108 is defined between the ends 104, 106. The cylinder 102 includes a cylinder wall 110 extending between the ends 104, 106, about a longitudinal axis L. A cap 112 is coupled to the cylinder 102 at the proximal end 104 and a piston 114 is disposed in the cylinder 102 at the distal end 106 such that the mixing chamber 108 is further defined between the cap 112 and the piston 114. The components of the bone cement are placed in the mixing chamber 108 and mixed by the mixing shaft 150 and blade 152, as will be described further below.

In the preferred embodiment, the cylinder 102 has locking strips 116 disposed on the cylinder wall 110 at the proximal end 104 to insert into locking slots 118 on the cap 112. Each of the locking strips 116 include a straight portion lying perpendicular relative to the longitudinal axis L and an angled portion lying at an angle relative to the straight portion. As should be appreciated, the locking strips 116 and locking slots 118 could be reversed, i.e., the locking strips 116 positioned on the cap 112 and the locking slots 118 defined in the cylinder wall 110. The locking strips 116 and locking slots 118 are configured to provide quick locking of the cap 112 onto the cylinder 102 with a one-quarter turn of the cap 112. Those of ordinary skill in the art will appreciate that numerous methods are available for connecting the cap 112 to the cylinder 102, such as mating threads, snap-fit connections, etc. A groove 120 is formed in the cylinder 102 at the proximal end 104 to seat an o-ring seal 122. The o-ring seal 122 assists in sealing the cap 112 to the cylinder 102.

Figure 3:
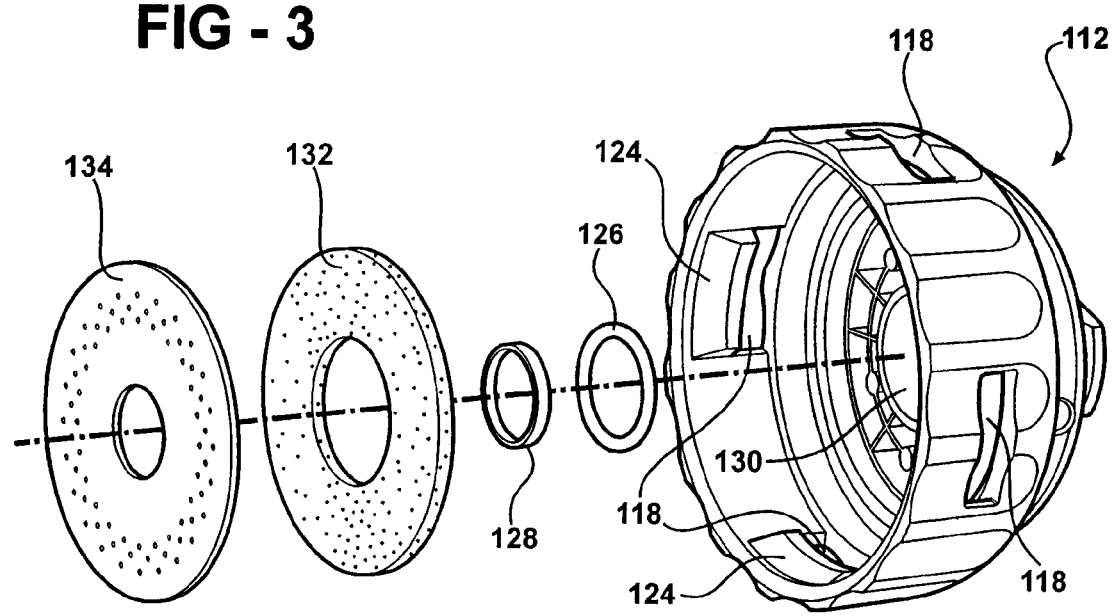
FIG. 3 is an exploded perspective view of a cap of the mixing cartridge.
Figure 4:
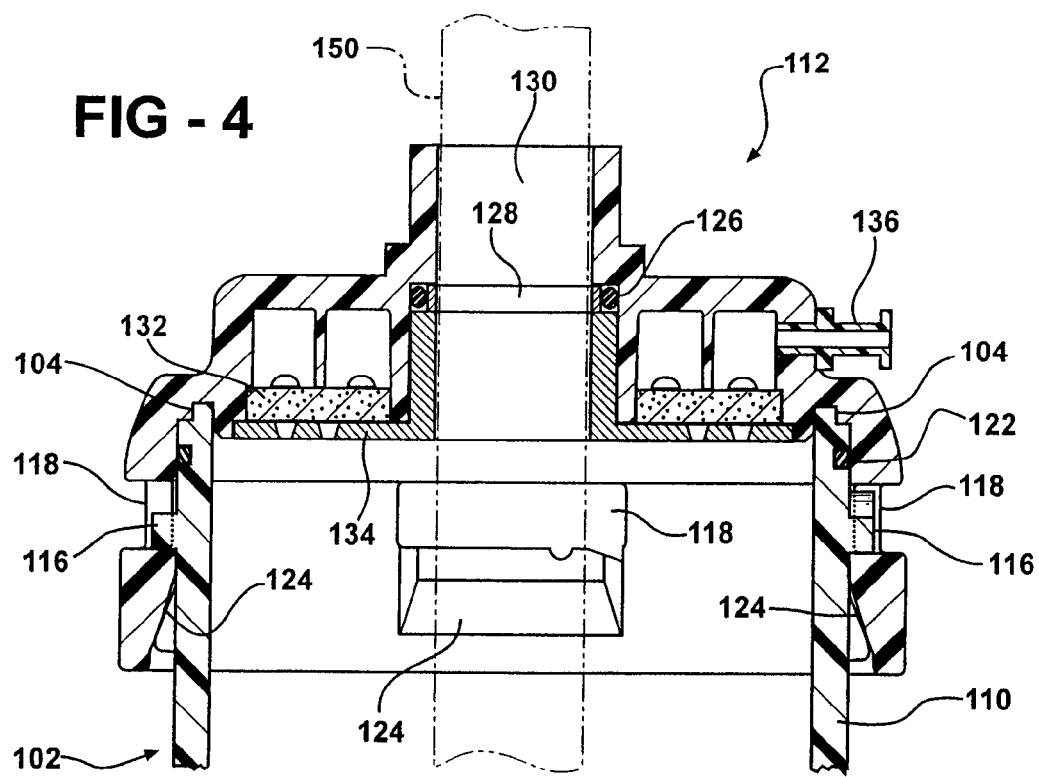
FIG. 4 is a cross-sectional view of the cap of FIG. 3 and a partial cross-sectional view of a cylinder of the mixing cartridge to illustrate fitting of the cap to the cylinder.

Referring to FIGS. 3-4, the cap 112 includes radially inwardly protruding ramps 124 that lead into the locking slots 118 to facilitate the fit with the locking strips 116 on the cylinder wall 110. When first placing the cap 112 on the cylinder 102, the locking strips 116 are positioned between the ramps 124. As the cap 112 is rotated, the ramps 124 cam the locking strips 116 proximally to urge the proximal end 104 of the cylinder 102 into a sealed relationship with the cap 112, as shown in FIG. 4 (only a portion of the cylinder wall 110 with two locking strips 116 is shown in FIG. 4 for illustrative purposes). In the preferred embodiment, there are four locking strips 116 and four locking slots 118 to facilitate the sealed relationship between the cap 112 and the cylinder 102.

Figure 5:
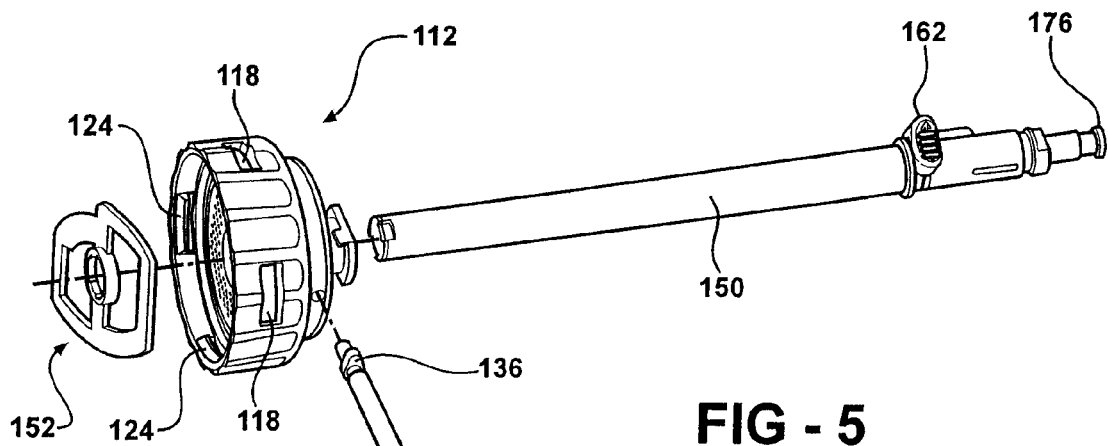
FIG. 5 is an exploded perspective view of the cap and the mixing shaft and blade.
Figure 6:
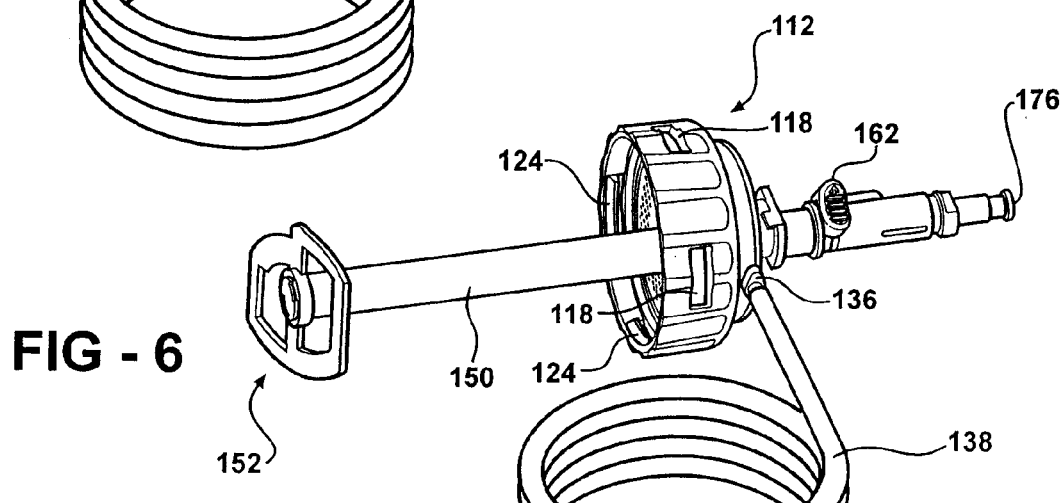
FIG. 6 is an assembled perspective view of the cap with the mixing shaft and blade supported therein.

Referring specifically to FIG. 4, an o-ring seal 126 and dynamic seal 128 operate together within an orifice 130 in the cap 112 to movably support and seal to the mixing shaft 150. The mixing shaft 150 slides through the orifice 130 and the dynamic seal 128 and is movably supported therein. The dynamic seal 128 allows nearly frictionless rotational, as well as axial movement of the mixing shaft 150 within the mixing chamber 108 to mix the liquid and powder components of the bone cement, while maintaining a snug fit within the orifice 130. A filter 132 and liner 134 are positioned on an interior of the cap 112 to allow a vacuum to be drawn in the mixing chamber 108 by way of a vacuum port 136. The vacuum port 136 is isolated from the mixing chamber 108 by the filter 132 and liner 134 to prevent fouling of a vacuum pump (not shown). Referring to FIGS. 5-6, a vacuum tube 138 is shown attached to the vacuum port 136 to draw the vacuum in the mixing chamber 108 during mixing.

Figure 7:
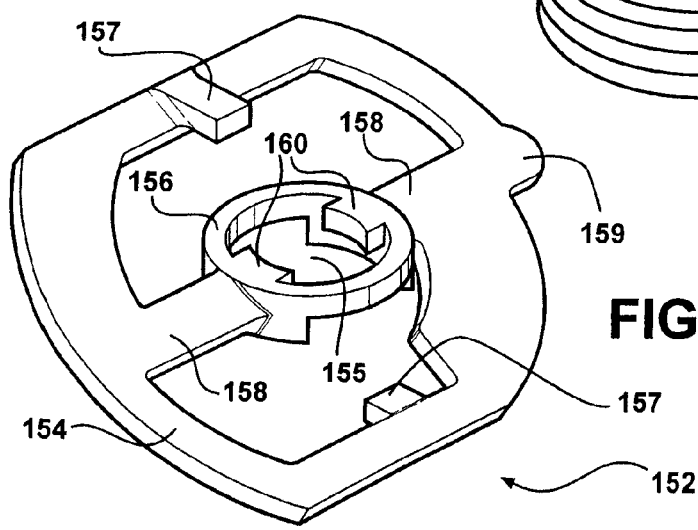
FIG. 7 is a perspective view of the blade.
Figure 7A:
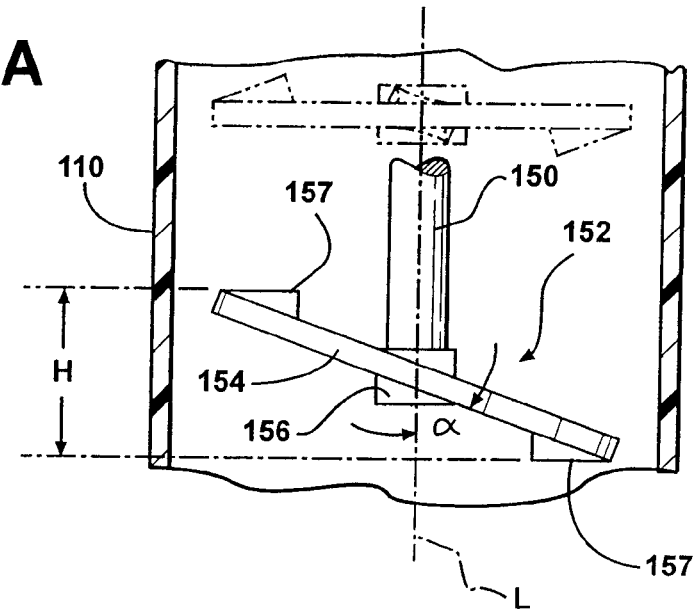
FIG. 7A is a side elevational view of the blade of FIG. 7.

Referring to FIG. 7, the preferred blade 152 used to mix the bone cement is shown. The blade 152 is integrally formed from plastic in one piece and has an outer ring 154 connected to a center hub 156 by vanes 158. Ears 160 protrude radially inwardly from the center hub 156 to facilitate a releasable connection to the mixing shaft 150. The releasable connection is described further below. Referring to FIG. 7A, the outer ring 154 forms an acute angle α with the longitudinal axis L of the cylinder 102 (which is also a rotational mixing axis of the blade 152). The acute angle a is important for efficient mixing of the bone cement. The acute angle α is preferably between twenty and seventy degrees, and more preferably sixty degrees. The blade 152 has an effective height H that is greater than one quarter inch to ensure adequate mixing. Preferably, the effective height H of the blade 152 is approximately one half inch.

Referring back to FIG. 7, two radially inwardly protruding fingers 157 are attached to the outer ring 154. One of the fingers 157 protrudes radially inwardly in a first plane and the other finger 157 protrudes radially inwardly in a second plane spaced from and parallel to the first plane. The center hub 156 is positioned between the planes. The fingers 157 are used to scrape proximal and distal regions of the mixing chamber 108 to ensure complete mixing. A protruding node 159 is also attached to the outer ring 154. The node 159 protrudes radially outwardly to control spacing between the blade 152 and an inner periphery of the cylinder wall 110 by scraping along the inner periphery of the cylinder wall 110 in the mixing chamber 108.

Figure 8:
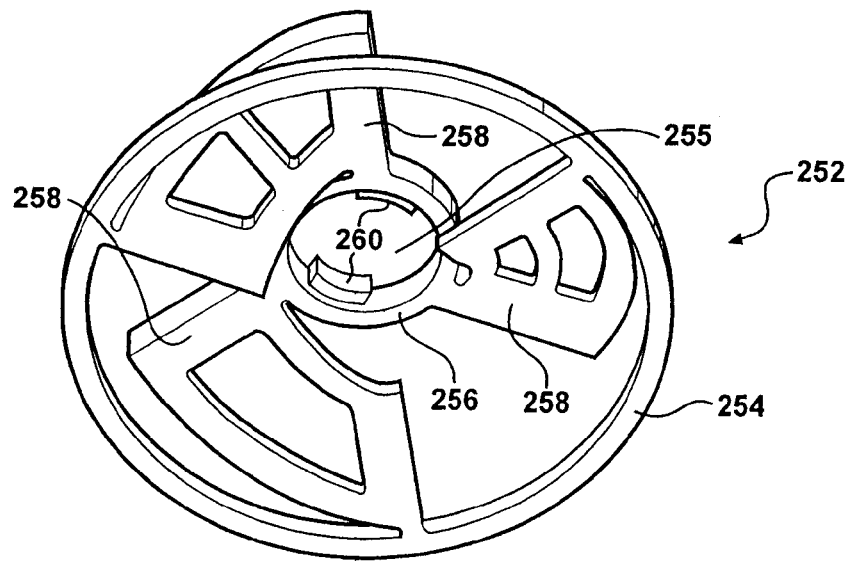
Figure 8A:
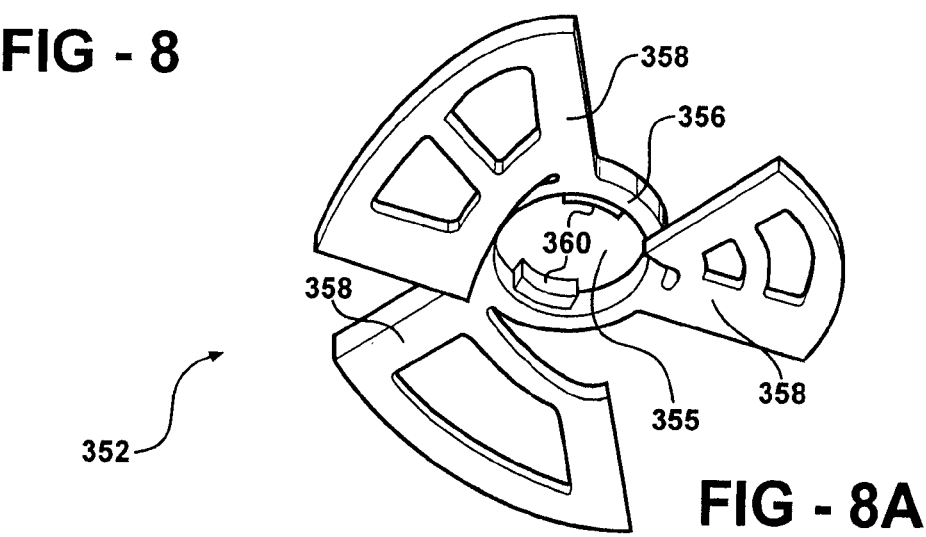

FIGS. 8 and 8A illustrate alternative blades 252, 352 that could also be used to mix the bone cement. Each of the blades 152, 252, 352 is designed to flatten at the proximal end 104 of the cylinder 102 adjacent to the cap 112 after the blade 152, 252, 352 is released from the mixing shaft 150 in the mixing chamber 108. This ensures that the maximum possible amount of bone cement can be discharged from the mixing cartridge 100. In the case of the preferred blade 152, the blade 152 is flexible and the outer wall 154 flattens into a plane perpendicular to the longitudinal axis L and occupied by the center hub 156, as illustrated by hidden lines in FIG. 7A. Thus, the effective height H is reduced and the acute angle α becomes close to ninety degrees. This is accomplished by twisting at the vanes 158. Spaces 155, 255, 355 formed in the center hub 156, 256, 356 ensure that once the blade 152, 252, 352 is flattened, the bone cement can pass through the blade 152, 252, 352 when discharged from the mixing cartridge 100. To further facilitate the discharge of the bone cement past the blades 152, 252, 352, each of the center hubs 156, 256, 356 are sized to partially fit within the aperture 130 defined in the cap 112.

Another alternative blade 452 is shown in FIG. 9. This blade 452 is a relatively thick disk 452 with chamfered ends 453 forming an acute chamfer angle with a sidewall 457. The chamfer angle is preferably sixty degrees. In the preferred embodiment, the disk is about one half inch thick and about one eighth inch less in diameter than the inner periphery of the cylinder wall 110. In one embodiment, the inner periphery of the cylinder wall 110 is about two and one quarter inches in diameter. As should be appreciated, the slight distance between the side wall 457 of the disk 452 and the inner periphery of the cylinder wall 110 creates a shear force on the bone cement as the disk 452 is rotated and moved axially in the mixing chamber 108. The shear force is the force applied to the bone cement to mix the bone cement. This blade 452 also includes a space 455 formed in a center of the disk 452 and ears 460 for releasably attaching to the mixing shaft 150.

Referring to FIGS. 10-13 the mixing shaft 150 has a release latch 162 for releasing the blade 152 from the mixing shaft 150 once mixing of the bone cement is complete. The release latch 162 moves between a holding position and a releasing position. In the holding position, the blade 152 is secured to the mixing shaft 150 to mix the bone cement in the mixing chamber 108. In the releasing position, the blade 152 is released from the mixing shaft 150 to remain in the mixing chamber 108 while the mixing shaft 150 is removed from the cap 112 to make way for a nozzle 204, as will be described further below. The release latch 162 is operatively connected to a latch rod 164, which latches the blade 152 to the mixing shaft 150 in the holding position. The latch rod 164 defines a split cavity 166 for receiving split legs 168 of the release latch 162 in a snap-fit manner. The latch rod 164 is rotatably supported within the mixing shaft 150.

Figure 14C:
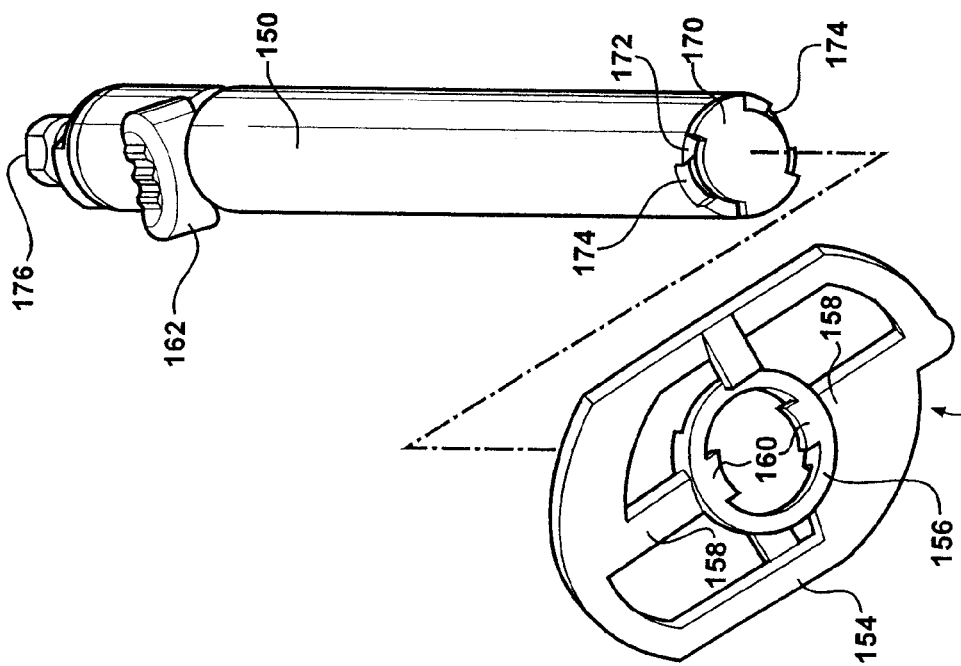
FIGS. 14A-14C illustrate the release of the blade from the mixing shaft.
Figure 14B:
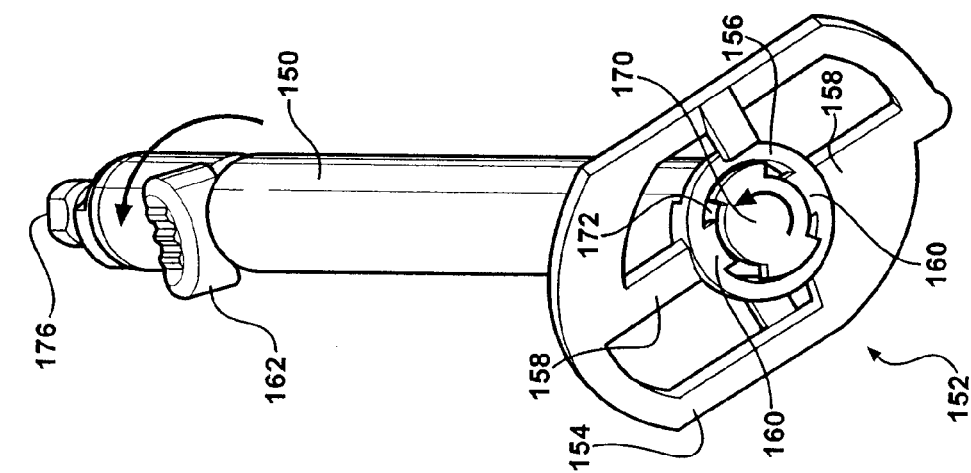
Figure 14A:
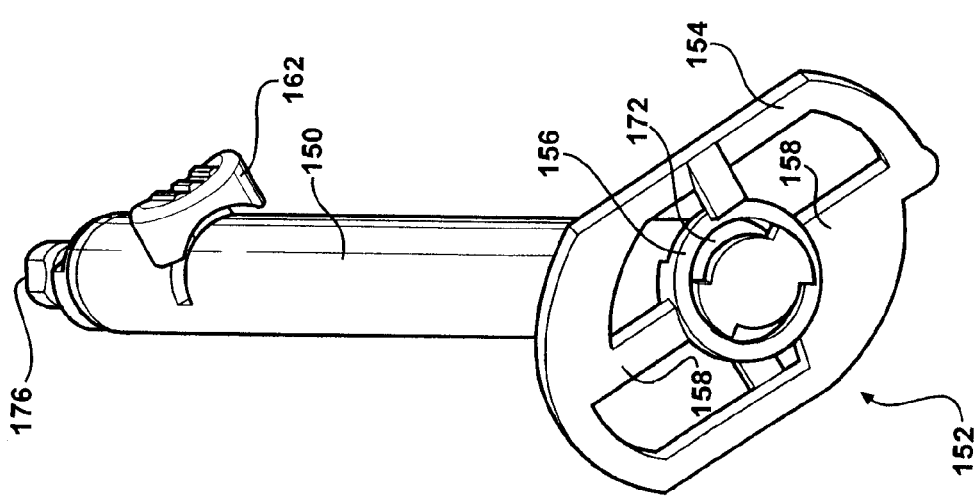

Referring to FIGS. 14A-14C, the transition of the release latch 162 between the holding position and the releasing position is illustrated. Referring first to FIG. 14C, the exposed end 170 of the latch rod 164 is generally "T" shaped. The corresponding end 172 of the mixing shaft 150 has opposed notches 174 that are adapted to receive the ears 160 on the center hub 156 of the blade 152. Initially, the ears 160 are positioned in the notches 174 and the exposed end 170 is positioned over the ears 160 to hold the blade 152 to the mixing shaft 150. See FIG. 14A. To release the blade 152, the release latch 162 is depressed and rotated. Rotating the release latch 162 rotates the latch rod 164 with respect to the mixing shaft 150 thus rotating the exposed end 170 away from the ears 160 to release the blade 152. See FIG. 14B. With the blade 152 released, the mixing shaft 150 is withdrawn from the cap 112 while the blade 152 remains in the mixing chamber 108.

A proximal end 176 of the mixing shaft 150, which represents a portion of the mixing shaft 150 extending outside of the mixing chamber 108 during mixing, is adapted to engage a rotary power tool 177 (see FIG. 37), such as a reamer drill, used to rotate the mixing shaft 150 and blade 152 and mix the bone cement. The proximal end 176 of the mixing shaft 150 is operatively connected to the blade 152 to transfer the rotation of the rotary power tool 177 to the blade 152. When the blade 152 is released from the mixing shaft 150, the operative connection is removed. The operative connection is also removed if the portion of the mixing shaft 150 extending outside of the mixing chamber 108 is severed from the rest of the mixing shaft 150 in the mixing chamber 108, as in alternative embodiments. A manually operated mixing handle (not shown) could engage the mixing shaft 150 at the proximal end 176 to mix the bone cement in other embodiments.

Figure 15:
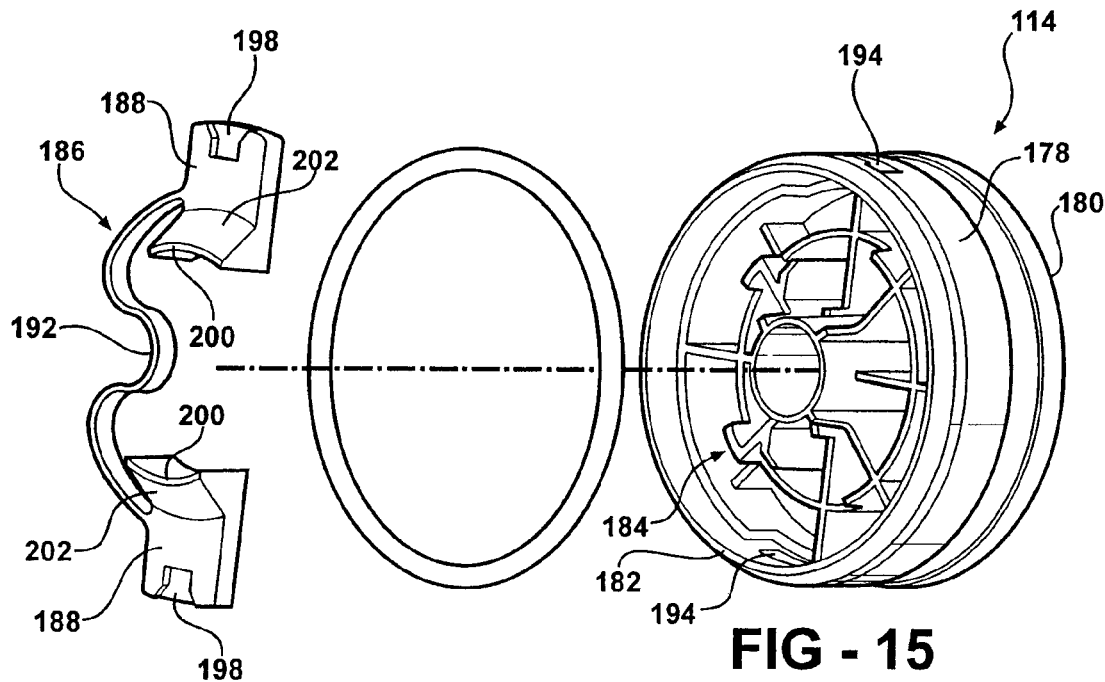
FIG. 15 is an exploded perspective view of a piston of the mixing cartridge.
Figure 16:
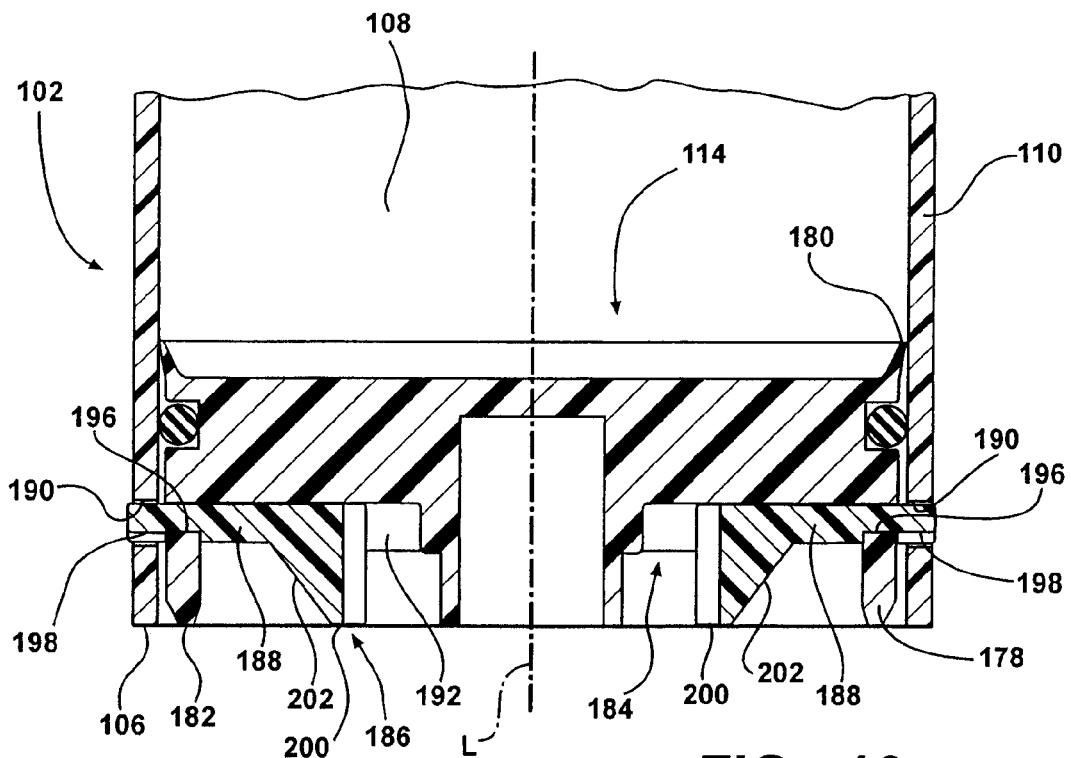
FIG. 16 is a cross-sectional view of the piston of FIG. 15.
Figure 19:
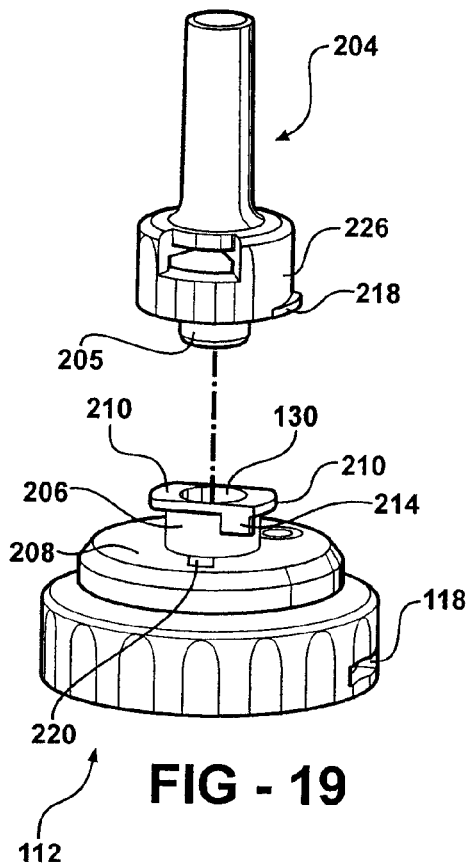
FIG. 19 is an exploded perspective view of the cap and a nozzle.
Figure 20:
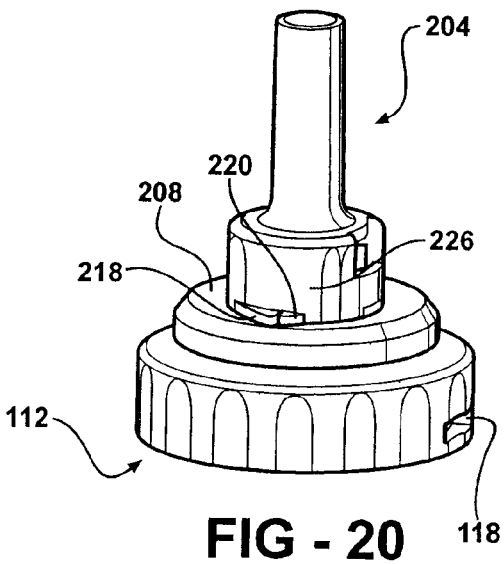
FIG. 20 is an assembled perspective view of the cap and nozzle.

Referring to FIGS. 15-16, the piston 114 is positioned within the distal end 106 of the cylinder 102 to further seal the mixing chamber 108. The piston 114 has a skirt 178 extending about the inner periphery of the cylinder wall 110. The piston 114 also includes a proximal end 180 and a distal end 182 defining a cavity 184.

Referring specifically to FIG. 16, the piston 114 is releasably secured in a locked position in the distal end 106 of the cylinder 102 by a locking member 186. The locking member 186 is disposed in the cavity 184 and includes diametrically opposed locking tabs 188 protruding into diametrically opposed slots 190 defined in the cylinder wall 110 to secure the piston 114 to the cylinder 102. It should be appreciated that the slots 190 could be in the form of any suitable female portion, e.g., slot, groove, channel, etc., used for interlocking with a corresponding male portion such as the locking tabs 188. Furthermore, while the embodiment of FIG. 16 illustrates two-way locking, i.e., the piston 114 being locked from moving proximally and distally, the locking member 186 could also be used for one-way locking, i.e., for preventing only proximal movement of the piston 114.

The locking member 186 is integrally formed from plastic and a resilient portion 192 of the locking member 186 biases the locking tabs 188 radially outwardly from the longitudinal axis L into the slots 190. The resilient portion 192 is in the form of a thin resilient ribbon 192 acting like a spring and extending is a winding shape between the locking tabs 188. The locking tabs 188 couple the locking member 186 to the piston 114 by protruding through carrier slots 194 formed in the skirt 178. In the preferred embodiment, a step 196 protrudes into each of the carrier slots 194 to define a guide for sliding engagement within a channel 198 partially defined in each of the locking tabs 188. In the locked position, the carrier slots 194 are axially and radially aligned with the slots 190 formed in the cylinder wall 110.

The piston 114 is locked at the distal end 106 of the cylinder 102 while the liquid and powder components are added and mixed in the mixing cartridge 100. The piston 114 is released from the locked position after mixing of the bone cement is complete. Release buttons 200, integrally formed with the locking tabs 188, are used to release the piston 114 from the locked position. The release buttons 200 are disposed on the locking tabs 188 and protrude distally therefrom. Each of the release buttons 200 includes a cam surface 202 forming an acute angle with the longitudinal axis L. The piston 114 is released from the locked position by squeezing the release buttons 200 radially inwardly against the bias of the resilient portion 192 to withdraw the locking tabs 188 from the slots 190. This action can be performed either manually or mechanically, as will be described further below. After release from the slots 190, the locking tabs 188 remain coupled to the piston 114 in the carrier slots 194.

Referring to FIGS. 17-18, an alternative locking member 386 is shown. The alternative locking member 386 includes locking tabs 388 that are biased radially outwardly from the longitudinal axis L of the cylinder 302 to engage the slots 390 in the cylinder wall 310. In this embodiment, four slots 390 are defined in the cylinder wall 310 to receive the locking tabs 388. The resilient portion 392 is further defined as a resilient base 392 resiliently supporting each of the locking tabs 388 on the piston 314 with each of the locking tabs 388 being radially biased outwardly from the skirt 378 of the piston 314 to engage the slots 390 in the cylinder wall 310. The release buttons 400 are further defined as fingers 400 extending radially inwardly toward the longitudinal axis L of the cylinder 302 with the fingers 400 being engageable to urge the locking tabs 388 radially inwardly and withdraw the locking tabs 388 from the slots 390 in the cylinder wall 310 to release the piston 314 from the locked position.

Referring to FIGS. 19-23, once the bone cement is mixed, and the mixing shaft 150 is withdrawn from the cap 112, the nozzle 204 is positioned on the cap 112. In the disclosed embodiment, the nozzle 204 is set in place by pushing a hollow shaft 205 of the nozzle 204 down into the orifice 130 of the cap 112 and then twisting the nozzle 204 slightly, about one-quarter turn. The nozzle 204 is attached to the cap 112 to prepare the mixing cartridge 100 for placement into the delivery gun 500.

The cap 112 has a nipple 206 protruding from an outer surface 208 thereof. The nipple 206 has tabs 210, which engage detent members 212 in the nozzle 204. After the nozzle 204 is fully rotated into position, the tabs 210 fully engage the detent members 212 while being positioned proximal to the detent members 212 to secure the nozzle 204 in place. A stop 214 on the cap 112, best shown in FIG. 19, prevents the nozzle 204 from rotating freely in the clockwise direction after the tabs 210 have engaged the detent members 212. The stop 214 extends downwardly from one of the tabs 210 to abut a side surface 216 of one of the detent members 212 to prevent further clockwise rotation.

Figure 21:
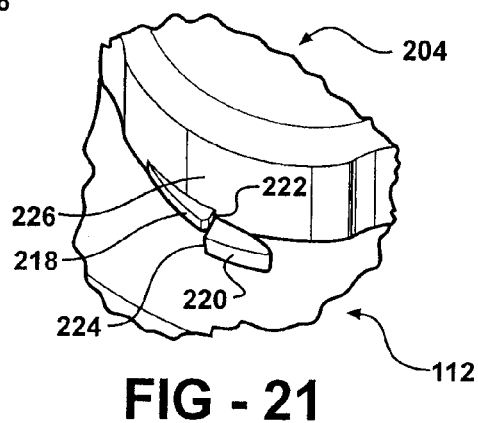
FIG. 21 is a blown-up view of a locking mechanism of the cap and nozzle.
Figure 22:
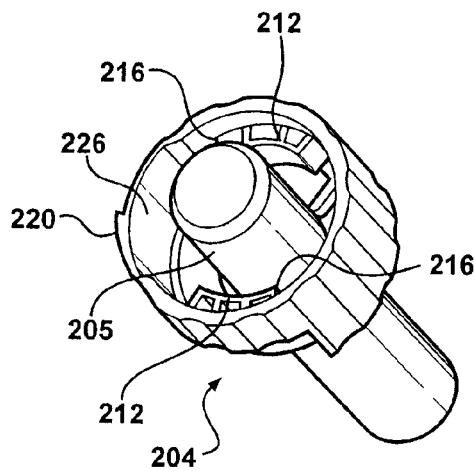
FIGS. 22-23 are perspective views of the nozzle.
Figure 23:
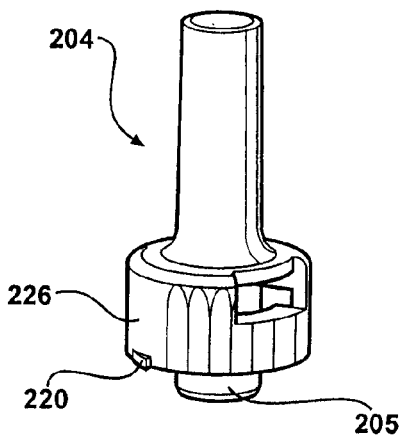

The nozzle 204 and cap 112 have first 218 and second 220 locking protrusions. The first locking protrusion 218 acts as a detent and slides over the second locking protrusion 220 to a locked position as illustrated in FIG. 21. In this position, rear flat surfaces 222, 224 of the locking protrusions 218, 220, abut one another to prevent the nozzle 204 from being turned in the opposite direction, thereby preventing removal of the nozzle 204 from the cap 112. The nozzle 204 can be removed by deflecting an outer skirt 226 of the nozzle 204 and rotating the nozzle 204 counterclockwise thereby disengaging the locking protrusions 218, 220. Both the nozzle 204 and cap 112 are formed from plastic, which facilitates the detent-like locking and unlocking of the nozzle 204 to the cap 112.

Figure 24:
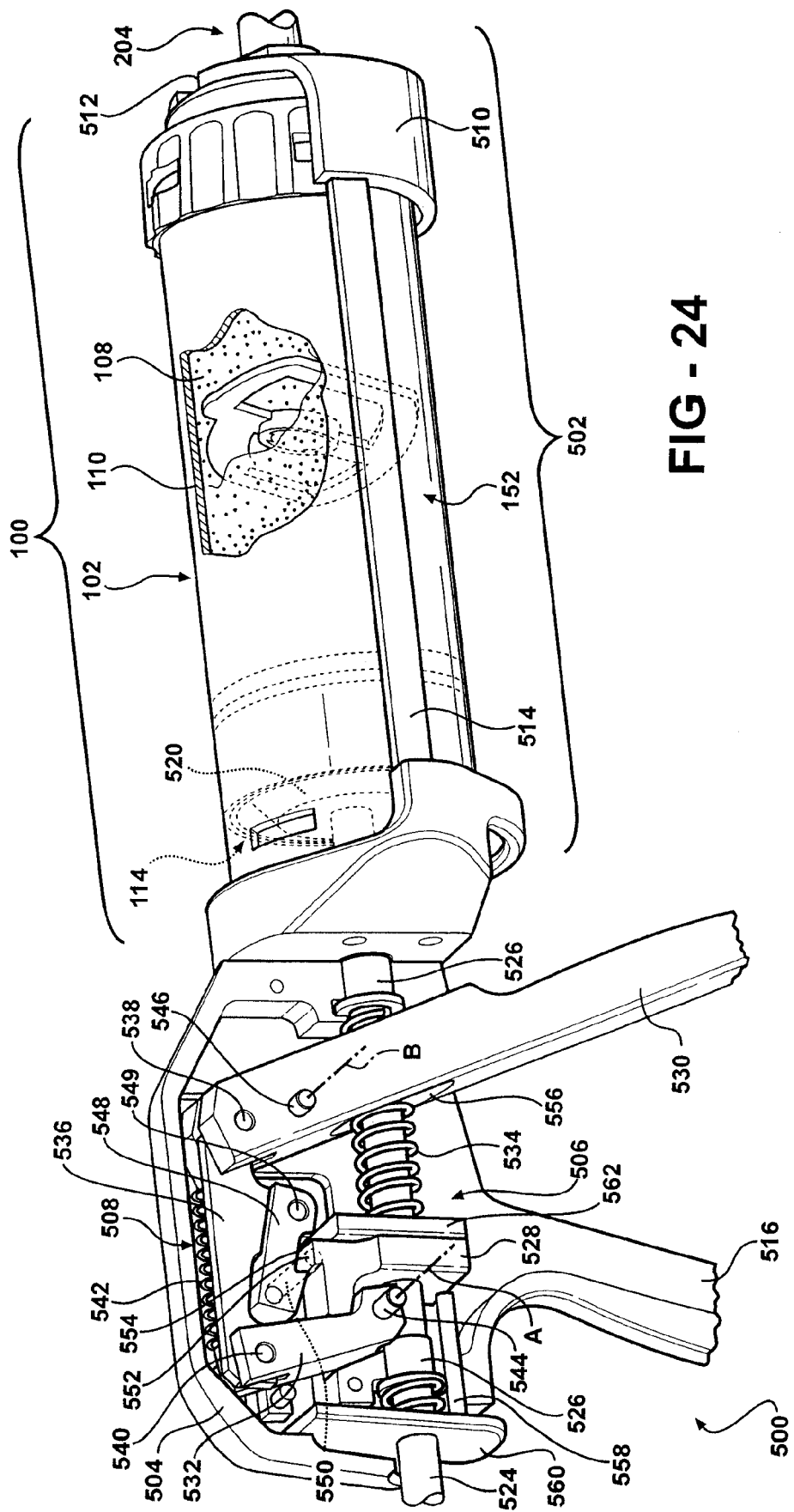
FIG. 24 is a perspective view of a delivery gun of the present invention illustrating a linkage system of the delivery gun.

With the nozzle 204 in place, the mixing cartridge 100 is ready to be placed within the delivery gun 500. Referring to FIG. 24, the delivery gun 500 of the present invention includes a cradle 502 for supporting the mixing cartridge 100 and a casing 504 fixed to the cradle 502 for supporting a drive mechanism 506, a linkage system 508, and corresponding components. The cradle 502 includes an endplate 510, which has an opening 512 for receipt of the nozzle 204. The endplate 510 holds the mixing cartridge 100 in position in the cradle 502. In the preferred embodiment, the casing 504 and the endplate 510 are connected by two connecting bars 514 (one on each side of the mixing cartridge 100) to reduce the weight of the delivery gun 500. A handle 516 is integrally formed with the casing 504 to maneuver the delivery gun 500 during use.

To dispense the bone cement from the mixing cartridge 100, the piston 114 must first be released from the locked position. Referring to FIG. 25, this is accomplished using a release mechanism 518 integrated into the delivery gun 500. Once the mixing cartridge 100 is in place in the cradle 502, a ram disk 520 protrudes into the cavity 184 in the distal end 182 of the piston 114. The release mechanism 518 is integrated into the ram disk 520. The release mechanism 518 includes a bearing surface 522 forming an acute angle with the longitudinal axis L for catching the release buttons 200 to cam the release buttons 200 radially inwardly. More specifically, the cam surfaces 202 of the release buttons 200 slide along the bearing surface 522, while being cammed radially inwardly. This action pulls the locking tabs 188 radially inwardly to withdraw the locking tabs 188 from the slots 190 in the cylinder wall 110 and release the piston 114 from the locked position (when the alternative piston 314 is used, the ram disk has a flat bearing surface that axially presses the fingers 400 proximally to bend each resilient base 392 inwardly and urge the locking tabs 388 radially inward). A centering pin 800 can be used to center the ram disk 520 in a centering cavity 802 of the piston 114 to facilitate the release of the piston 114 from the locked position.

Referring back to FIG. 24, once the piston 114 is released, the piston 114 can be driven through the mixing chamber 108 by the drive mechanism 506 to force the bone cement from the nozzle 204. The drive mechanism 506 includes a drive rod 524 movably supported by bushings 526 in the casing 504. The ram disk 520 is fixed to the drive rod 524. The drive mechanism 506 further includes a first gripper plate 528 responsive to movement of the linkage system 508 upon actuation of a trigger 530. The first gripper plate 528 defines an aperture surrounding the drive rod 524. The first gripper plate 528 frictionally engages the drive rod 524 to advance the drive rod 524. The first gripper plate 528 is urged forward while in frictional contact with the drive rod 524 by the linkage system 508 when the trigger 530 is actuated. The first gripper plate 528 thereby advances the drive rod 524 and ram disk 520 relative to the casing 504 to drive the piston 114 and force the bone cement from the mixing cartridge 100. The trigger 530 is pivotally supported by the casing 504 and operatively connected to the drive mechanism 506 to advance the drive mechanism 506 upon actuation of the trigger 530.

The linkage system 508 includes a first link 532, which is pivotally mounted to the casing 504 about a pivot axis A adjacent to the first gripper plate 528. The first link 532 is adapted to engage the first gripper plate 528 when the first link 532 pivots about the pivot axis A. A second link 536 pivotally interconnects the trigger 530 to the first link 532 via support pins 538, 540. The links 532, 536 and trigger 530 are interconnected to move in unison upon rotation of the trigger 530 about a second pivot axis B. When the trigger 530 is pulled, the second link 536 rotates the first link 532 about the pivot axis A, which engages the first gripper plate 528 and urges the first gripper plate 528 forward while the first gripper plate 528 is in frictional engagement with the drive rod 524 thereby advancing the drive rod 524. A return spring 542 returns the links 532, 536 and the trigger 530 to an initial position upon release of the trigger 530. At the same time, a first spring 534 momentarily disengages the first gripper plate 528 from the drive rod 524 to slide the first gripper plate 528 back to an initial position to await the next pull of the trigger 530. The casing 504 pivotally supports the first link 532 and the trigger 530 about the pivot axes A and B via support pins 544, 546.

A speed-changing link 548 is pivotally connected to the second link 536 about a support pin 549. The speed-changing link 548 selectively pivots into and out from engagement with the first gripper plate 528 by way of a switch 550. The speed-changing link 548 pivots between a high-speed position and a low-speed position about the support pin 549 (the low-speed position is shown in FIG. 24). The high-speed position corresponds to faster advancement of the drive rod 524 at a lower force. This allows the user to quickly advance the drive rod 524 to drive the piston 114 and dispense high volumes of bone cement at low pressure. The low-speed position corresponds to slower advancement of the drive rod 524 at a higher force, which exerts more force on the piston 114 to pressurize the bone cement.

The first gripper plate 528 and the speed-changing link 548 have complementary first and second coupling devices 552, 554 used to couple the first gripper plate 528 with the speed-changing link 548 in the high-speed position. More specifically, in the embodiment of FIG. 24, the first gripper plate 528 has a shoulder 552 that is received within a channel 554 on the speed-changing link 548. The speed-changing link 548 engages the shoulder 552 in the high-speed position. In the high-speed position, a user's gripping force is transmitted through the trigger 530 to the second link 536 and the speed-changing link 548 to engage the first gripper plate 528 and advance the drive rod 524. The speed-changing link 548 is isolated from the first gripper plate 528 in the low-speed position. The low-speed position corresponds to the speed-changing link 548 being switched or disconnected from the shoulder 552. In the low-speed position, the user's gripping force is transmitted through the trigger 530 to both the first 532 and second 536 links to engage the first gripper plate 528 and advance the drive rod 524. This results in slower advancement of the drive rod 524, but at a much higher mechanical advantage than the high-speed position. As a result, the user can better pressurize the bone cement during injection.

The pivot axes A and B and the links 532, 536, 548 are positioned above the drive rod 524, while the trigger 530 extends below the drive rod 524. A channel 556 defined in the trigger 530 facilitates this configuration. There are several advantages to this configuration. Moving the second pivot axis B away from a user's hand results in better usage of the stronger index and ring fingers by allowing those fingers more travel distance as the trigger 530 is actuated. This configuration also allows the handle 516 to be closer to the drive rod 524, which is believed to reduce wrist strain when the user pushes the delivery gun 500 forward during cement pressurization. Another benefit is that it allows for a more streamlined casing design and better weight distribution.

In one embodiment, shown in FIG. 24, a secondary gripper plate 562 is mounted about the drive rod 524 adjacent to the first gripper plate 528. The addition of one or more secondary gripper plates 562 to the first gripper plate 528 adds strength to the delivery gun 500 while still permitting proper operation. By using two or more gripper plates 528, 562, increased frictional contact with the drive rod 524 is obtained without adversely affecting performance.

A release pin 558 disengages the gripper plates 528, 562 to allow a user to freely move the drive rod 524 by hand. The release pin 558 is connected to a retainer plate 560 and is adapted to engage the first gripper plate 528. When the retainer plate 560 is pushed by the user, the release pin 558 engages the first gripper plate 528 which forces the first gripper plate 528 to tilt back against the bias of the first spring 534 thus releasing the drive rod 524. Any secondary gripper plates 562 follow. As should be appreciated, pushing the retainer plate 560 also pivots the retainer plate 560 releasing its engagement with the drive rod 524. With both the retainer plate 560 and the gripper plates 528, 562 released, the drive rod 524 is free to move. This allows the user to manually move the drive rod 524 with respect to the casing 504.

The delivery gun 500 is unique among bone cement guns with a friction-plate mechanism in the way that it handles wear and deformation of the gripper plates 528, 562. In the disclosed embodiments, the gripper plates 528, 562 are tilted by the first spring 534 into frictional contact with the drive rod 524. Regardless of the amount of wear or deformation of the gripper plates 528, 562 or the drive rod 524, the gripper plates 528, 562 require no further tilting to engage the drive rod 524 upon actuation of the trigger 530. Thus, advancement of the drive rod 524 is produced over the entire actuation of the trigger 530 and efficiency is maintained throughout the life of the delivery gun 500.

Figure 24A:
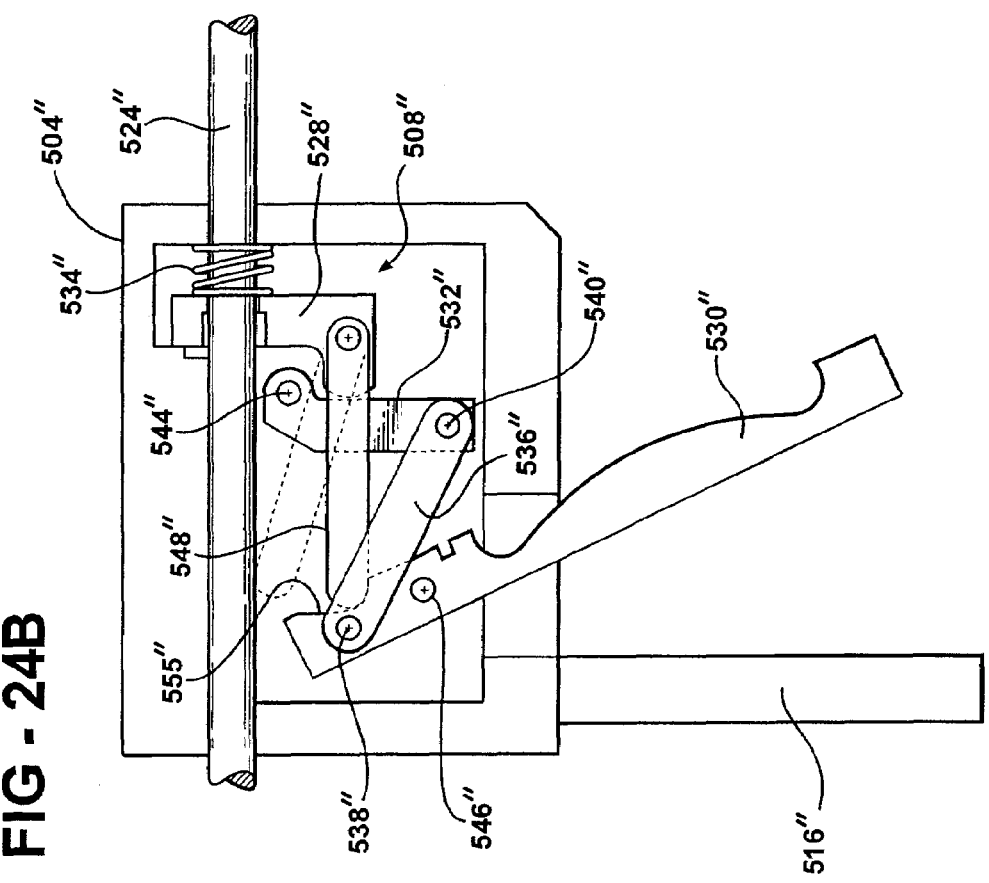
FIGS. 24A-24B illustrate alternative linkage systems of the present invention.
Figure 24B:
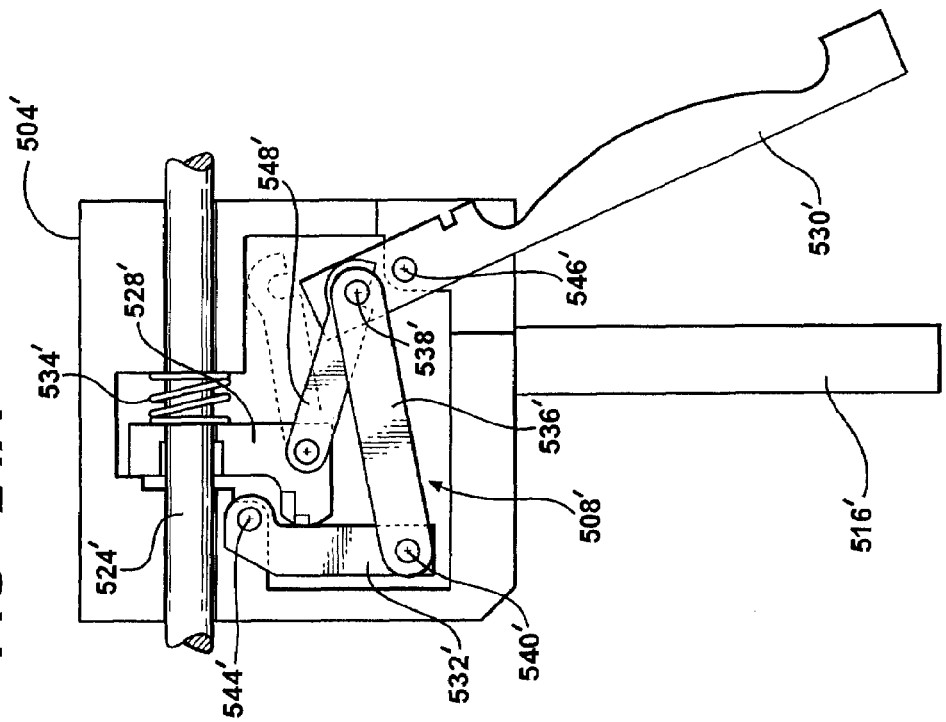

Referring to FIGS. 24A and 24B, alternatives of the linkage system 508' and 508" are shown. These alternatives are represented with similar numerals to the embodiment of FIG. 24 to indicate like parts. FIG. 24A illustrates a configuration of the linkage system 508' in which the linkage system 508' lies beneath the drive rod 524'. Furthermore, the speed-changing link 548' in this embodiment is pivotally connected to the first gripper plate 528' and includes a hook-shaped end to engage the support pin 538' in the high-speed position and disengage the support pin 538' in the low-speed position. FIG. 24B illustrates a configuration of the linkage system 508" in which the first gripper plate 528" is pushed by the linkage system 508", as opposed to being pulled by the linkage system 508 and 508' in FIGS. 24 and 24A. Here, the speed-changing link 548" is pivotally connected to the first gripper plate 528" to pivot into engagement with a notch 555" defined in the trigger 530" in the high-speed position and out from engagement with the notch 555" in the low-speed position. These alternatives of the linkage system 508' and 508" illustrate the flexibility of design, e.g., the selection of mechanical advantage, provided by the linkage system of the present invention.

Figure 26:
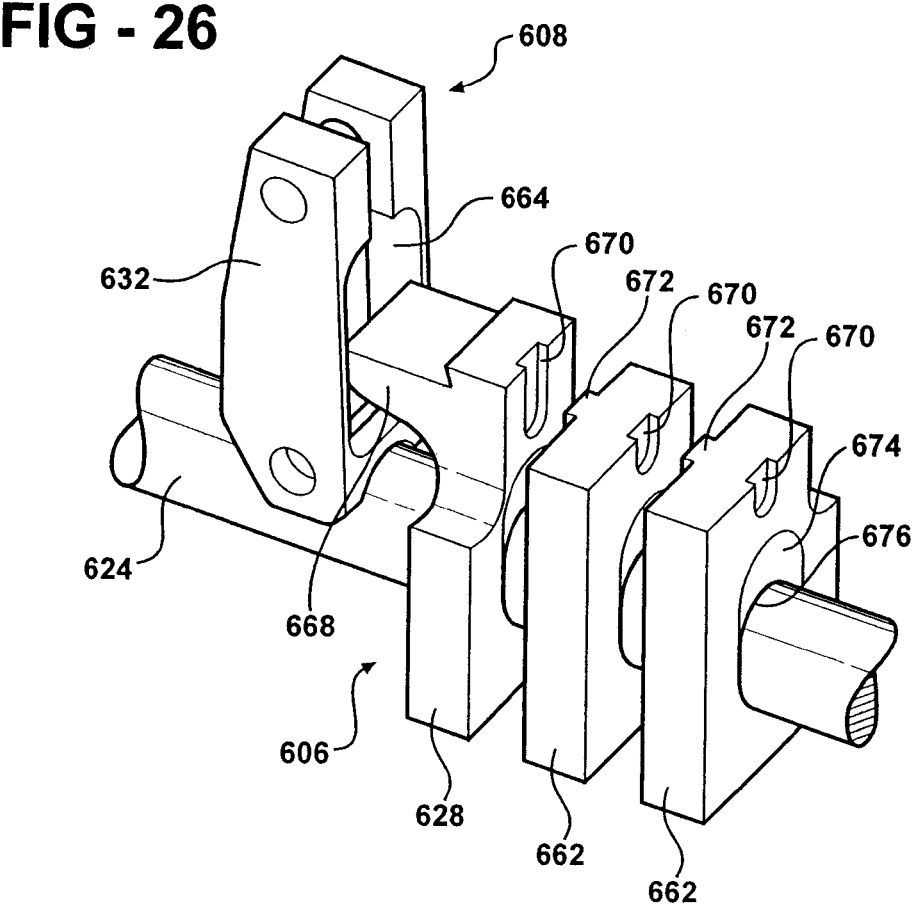
FIG. 26 is a partial perspective view of an alternative linkage system and drive mechanism of the delivery gun.
Figure 27:
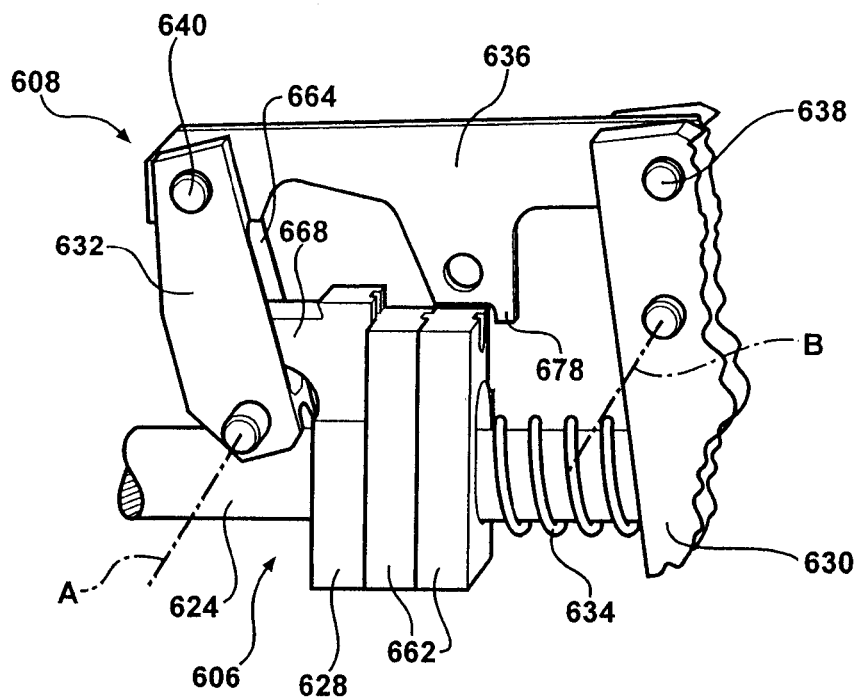
FIG. 27 is a partial perspective view of the alternative linkage system and drive mechanism of FIG. 26 employing a striker to prevent freeze-up of the drive mechanism.

Referring to FIGS. 26-27, an alternative embodiment of the drive mechanism 606 and linkage system 608 is shown (only a portion of the drive mechanism 606 and linkage system 608 is shown for illustrative purposes). In this embodiment, the linkage system 608 comprises the same components as previously described with an improved first link 632 and gripper plates 628, 662. In this embodiment, a plurality of secondary gripper plates 662 are aligned along the drive rod 624 next to the first gripper plate 628. The first link 632 defines a female recess 664 and the first gripper plate 628 includes a male member 668 for mating engagement with the female recess 664. The secondary gripper plates 662 are aligned relative to the first gripper plate 628 via mating notches 670 and pegs 672 formed therein. The notches 670 and pegs 672 assume the same shape to mate with one another and maintain alignment. This arrangement minimizes alignment changes that may cause slipping or uneven wear. The arrangement also reduces contact between the gripper plates 628, 662 and an interior wall of the casing 504. The gripper plates 628, 662 are shown spaced in FIG. 26 for illustration only. In practice, the gripper plates 628, 662 abut one another, as shown in FIG. 27.

In this embodiment, each of the gripper plates 628, 662 also defines a pair of semi-spherical grooves 674. In FIG. 26, only the first of the pair of grooves 674 are shown in each of the gripper plates 628, 662. The other of the pair of grooves 674 is located in a rear surface of each of the gripper plates 628, 662, cater-cornered from the first of the pair of grooves 674. These grooves 674 increase the frictional contact with the drive rod 624. When the gripper plates 628, 662 are urged forward while in frictional engagement with the drive rod 624 by the first link 632, a substantial portion of a rim 676 defined by each of the grooves 674 frictionally contacts the drive rod 624.

Referring to FIG. 27, autoclave sterilization of the delivery gun 500 can create a tendency for the gripper plates 628, 662 to adhere to the drive rod 624 beyond their initial positions when the trigger 630 is released. In this situation the first spring 634 cannot produce enough force to disengage the gripper plates 628, 662 from the drive rod 624, and the gripper plates 628, 662 do not return to their initial positions. FIG. 27 shows a way to prevent this condition. A striker 678, in the form of a downwardly protruding portion of the second link 636, closely follows one of the gripper plates 628, 662 during actuation of the trigger 630. In the event that any of the gripper plates 628, 662 do not properly disengage the drive rod 624 upon release of the trigger 630, the striker 678 will contact the notch 670 in the closest gripper plate 628, 662 and dislodge the gripper plate 628, 662 from the drive rod 624. The first spring 634 can then properly return the gripper plates 628, 662 to their initial positions.

A coating has been added to an exterior of each of the gripper plates 528, 562, 628, 662 in FIGS. 24 and 26-27. The coating increases lubricity and corrosion resistance. This facilitates sliding between the gripper plates 528, 562, 628, 662 as they engage the drive rod 524, 624. The coating also reduces corrosion due to autoclave sterilization that may cause the gripper plates 528, 562, 628, 662 to adhere to one another and prevent proper engagement with the drive rod 524, 624. The coating used may be Electroless-Nickel with polytetrafluoroethylene (PTFE) or other like coatings possessing the same or similar properties.

Referring to FIGS. 28-31, another alternative embodiment of the drive mechanism 706 and linkage system 708 is shown. This embodiment also provides selective high-speed and low-speed advancement of the drive rod 724. This alternative drive mechanism 706 eliminates the gripper plate by providing teeth 780 on the drive rod 724. A cross-section of the drive rod 724 shows the teeth 780 on a flat upper surface 782, while a lower surface 784 is smooth and round. The first link 732, which in previous embodiments urged the first gripper plate 528, 628 forward with the drive rod 524, 624, now pivotally supports a first pawl member 786. The first pawl member 786 is spring-biased into engagement with the teeth 780.

Figure 28:
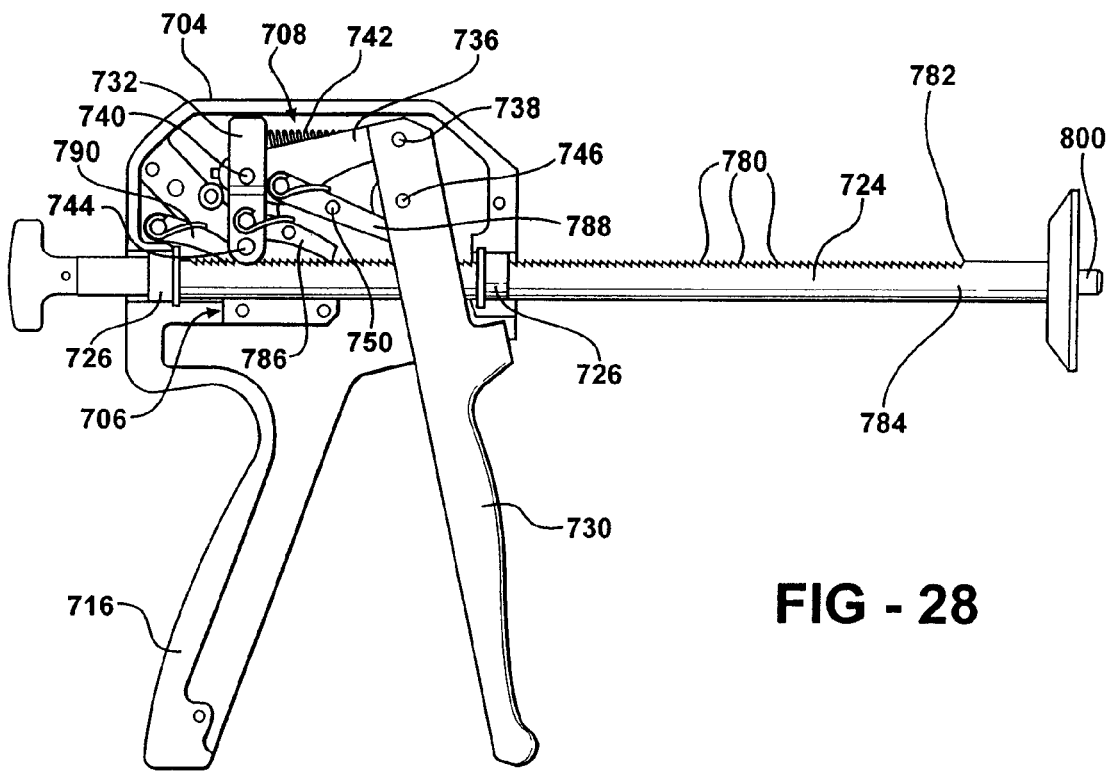
FIG. 28 is an elevational view of a second alternative embodiment of the linkage system and drive mechanism of the delivery gun in a low-speed position.
Figure 29:
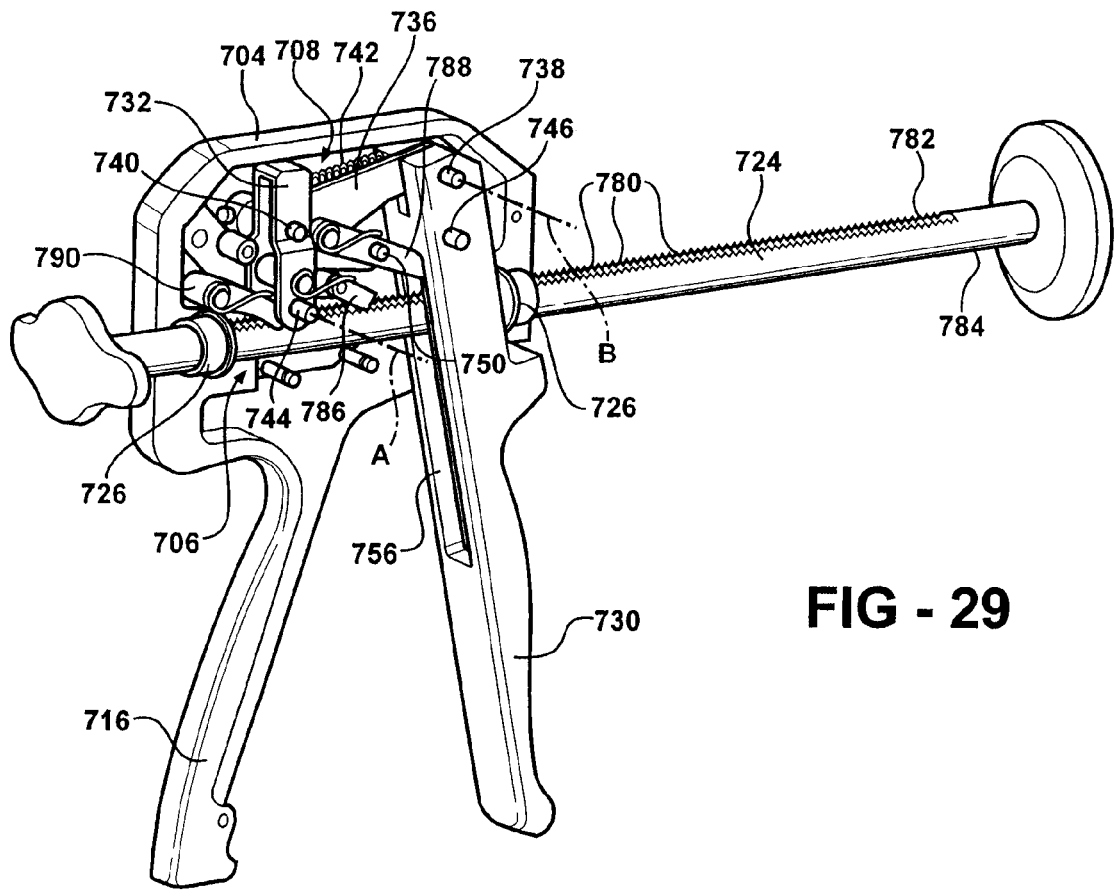
FIG. 29 is a perspective view of the second alternative embodiment of the linkage system and drive mechanism in the low-speed position.
Figure 30:
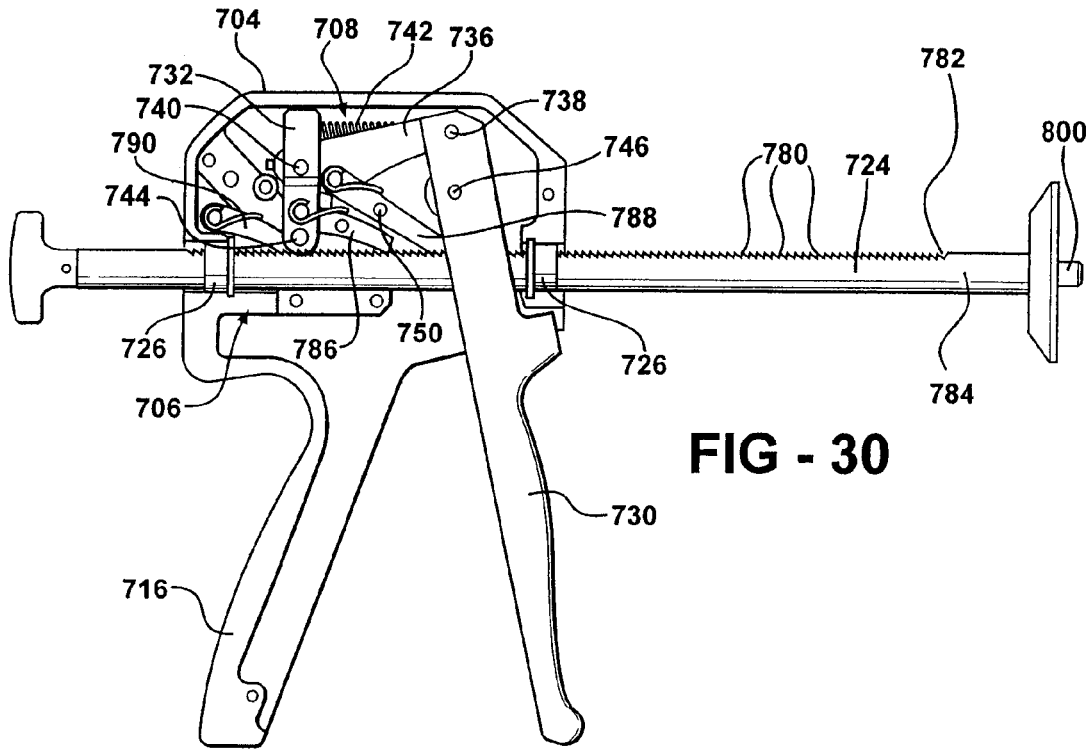
FIG. 30 is an elevational view of the second alternative embodiment of the linkage system and drive mechanism in a high-speed position.
Figure 31:
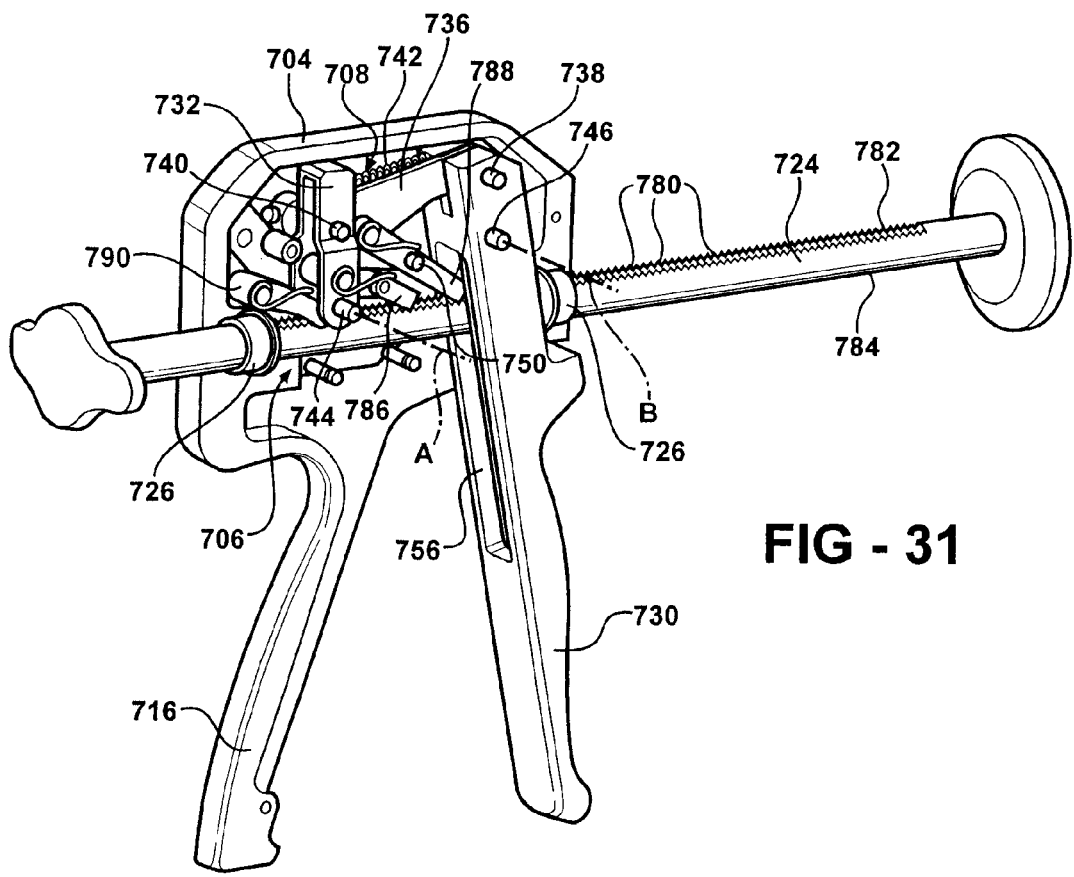
FIG. 31 is a perspective view of the second alternative embodiment of the linkage system and drive mechanism in the high-speed position.

A second pawl member 788 is pivotally supported by the second link 736. The second pawl member 788 is pivotable between a high-speed position in which the second pawl member 788 is spring-biased into engagement with the teeth 780 to advance the drive rod 724, and a low-speed position in which the second pawl member 788 is disengaged and isolated from the teeth 780. In the low-speed position, the first pawl member 786 advances the drive rod 724. The low-speed position is illustrated in FIGS. 28-29. In the high-speed position, with the second pawl member 788 engaging the teeth 780, the first pawl member 786 remains in engagement with the teeth 780, but only ratchets along the teeth 780 as the second pawl member 788 advances the drive rod 724. The high-speed position is illustrated in FIGS. 30-31. The principle of increasing mechanical advantage in the low-speed position relative to the high-speed position also applies in this embodiment.

The switch 750 is used to pivot the second pawl member 788 out from engagement with the teeth 780 of the drive rod 724 in the low-speed position (see FIGS. 28-29) and into engagement with the teeth 780 in the high-speed position (see FIGS. 30-31). A switch similar to that shown in U.S. Pat. No. 5,431,654 to Nic, herein incorporated by reference, can be used for this purpose. The switch 750 extends through the casing 704 and terminates in a button that is manipulated by a user to move the second pawl member 788 between the high-speed and low-speed positions (see briefly FIGS. 41-42). This also applies to the switch 550 used to move the speed-changing link 548 in previous embodiments.

In this embodiment, the retainer plate 560 can be removed. In its place, a spring-biased non-return pawl member 790 retains the drive rod 724 in position upon advancement. The drive rod 724 can be freely moved in the casing 704 by rotating the drive rod 724 one hundred and eighty degrees such that the pawl members 786, 788, 790 are out of engagement with the teeth 780. Upon such rotation, the pawl members 786, 788, 790 ride on the smooth lower surface 784 of the drive rod 724 allowing the user to freely pull the drive rod 724 relative to the casing 704. This is generally disclosed in the '654 patent to Nic.

Each of the pawl members 786, 788, 790 are pivotally supported by pins. Springs, such as those shown in the '654 patent to Nic, bias the pawl members into engagement with the teeth 780 on the drive rod 724 (except when the switch 750 acts against the bias of the spring in the low-speed position to disengage the second pawl member 788 from the teeth 780).

Figure 32:
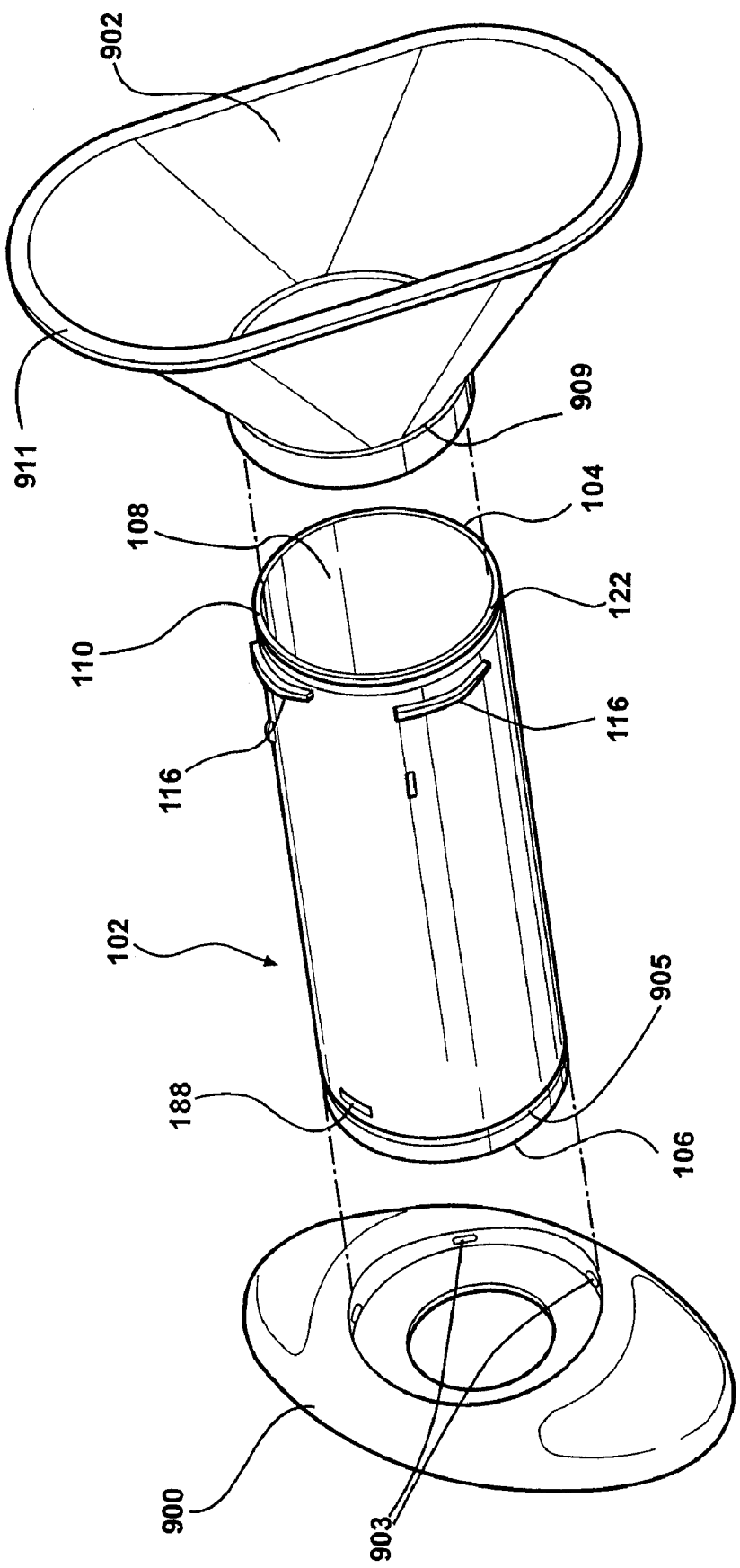
FIG. 32 is an exploded view of a cylinder of the mixing cartridge and a base and funnel used to fill the cylinder with components of bone cement.

Mixing and delivery of the bone cement will now be described with reference to FIGS. 32-42. Referring first to FIG. 32, a bone cement loading system is shown. The bone cement loading system comprises a base 900 supporting the cylinder 102 while loading the liquid and powder components of the bone cement into the mixing chamber 108. The base includes a cavity for receiving the distal end 106 of the cylinder 102. Detents 903 are formed in the cavity. A groove 905 is defined in an outer surface of the cylinder 102 to receive the detents 903 and facilitate a snug fit between the base 900 and the cylinder 102. It should be appreciated that the detents 903 could be formed on the cylinder 102 with the groove 905 defined in the base 900. The distal end 106 of the cylinder 102 may also be press fit into the base 900. The base 900 is oblong and oval in shape to fully support the cylinder 102 on a work surface, while the cavity is circular in shape to fit the circular shaped cylinder 102. A funnel 902 couples to the cylinder 102 to channel the powder into the cylinder 102 during loading. The funnel 902 includes a proximal end 911 having an oblong oval-shaped periphery to facilitate the loading of the powder into the mixing chamber 108 and a distal end 909 having a circular periphery to snugly fit inside the proximal end 104 of the cylinder 102.

FIGS. 33-42 illustrate ten steps for preparing and injecting the bone cement. The mixing cartridge 100, delivery gun 500, and other components are generically shown in each step for illustrative purposes only.

Figure 33:
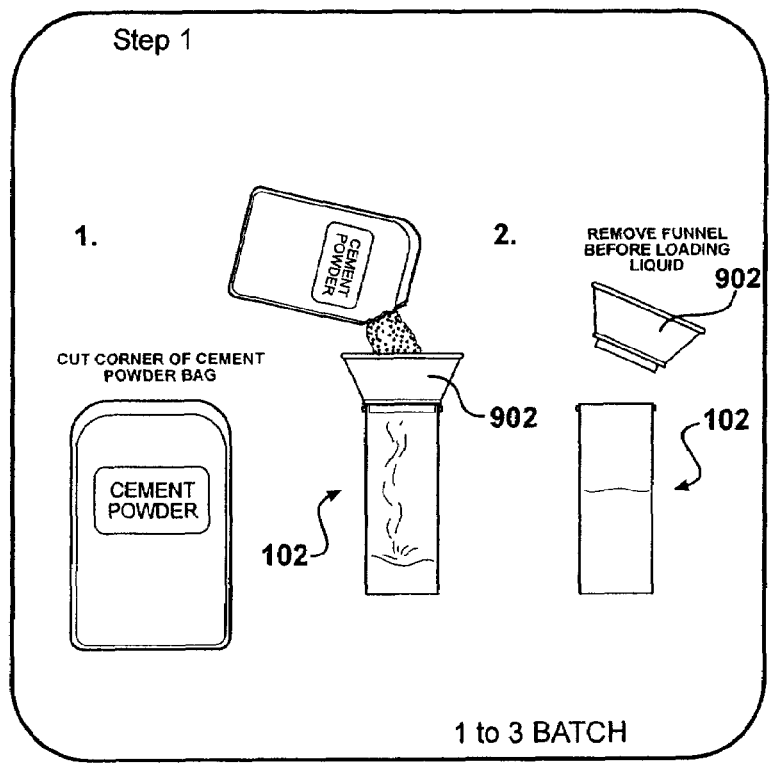
FIGS. 33-42 illustrate various steps associated with the present invention.

In STEP 1, shown in FIG. 33, the funnel 902 is coupled to the cylinder 102 and the powder is poured into the mixing chamber 108.

Figure 34:
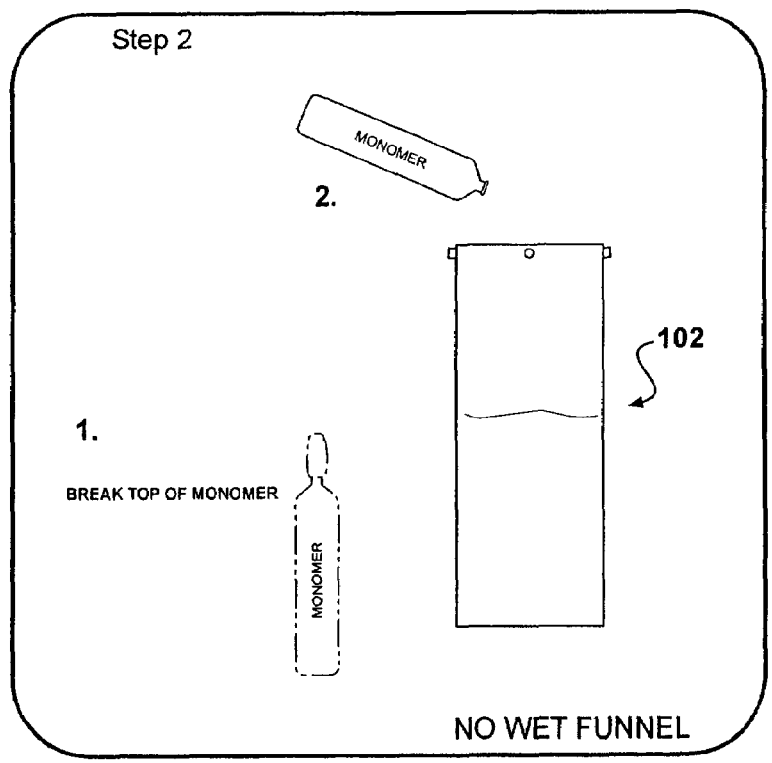

In STEP 2, shown in FIG. 34, after the powder is poured into the mixing chamber 108, the funnel 902 is removed, and the liquid component, e.g., liquid monomer, of the bone cement is added. In this manner, the present invention avoids wetting of the funnel 902 and the associated clean-up.

Figure 35:
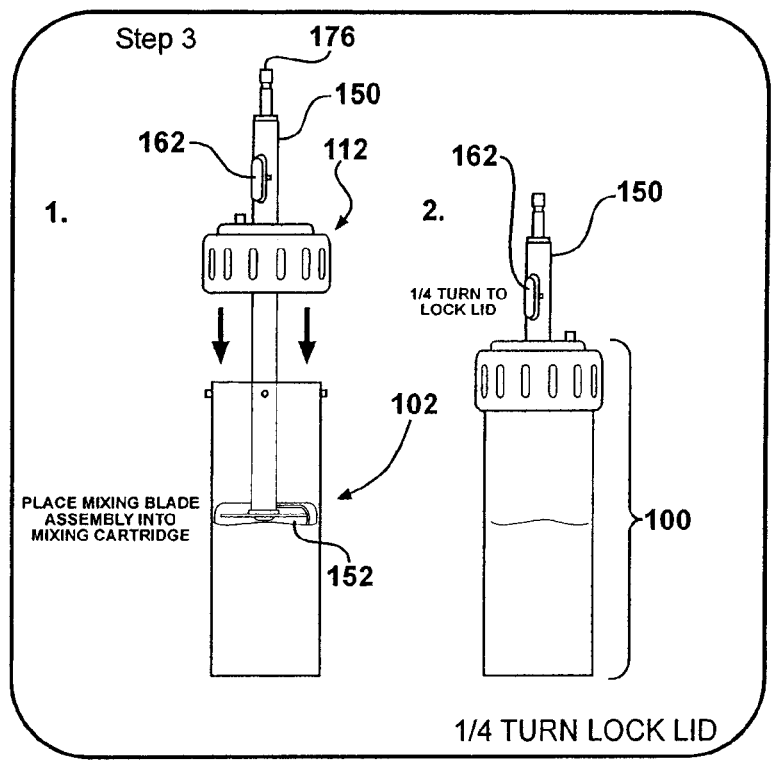

In STEP 3, shown in FIG. 35, the cap 112 with the mixing shaft 150 and blade 152 supported therein is attached to the cylinder 102.

Figure 36:
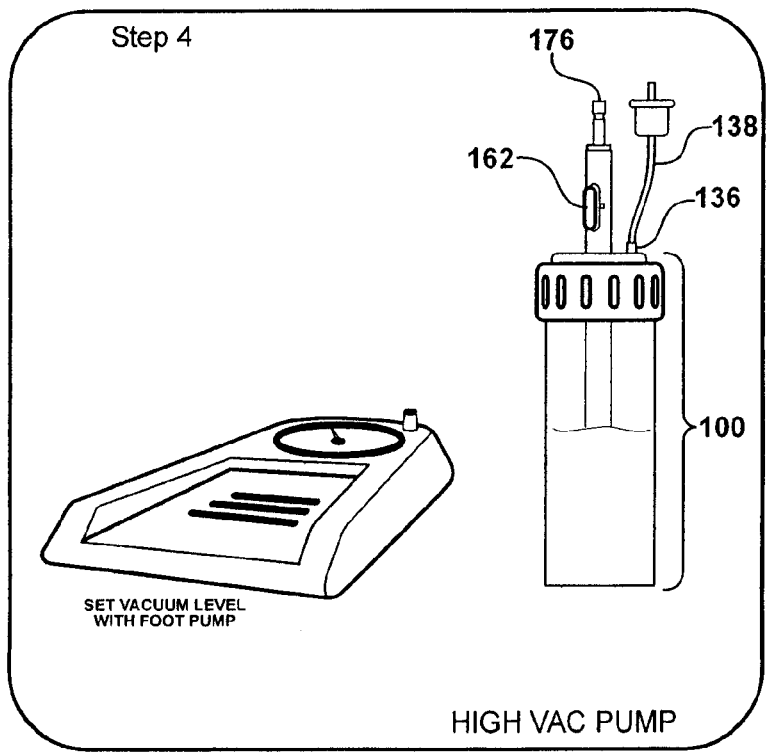

In STEP 4, shown in FIG. 36, the vacuum line 138 is attached to the vacuum port 136 and a vacuum is drawn in the mixing chamber 108 with the liquid and powder components therein.

Figure 37:
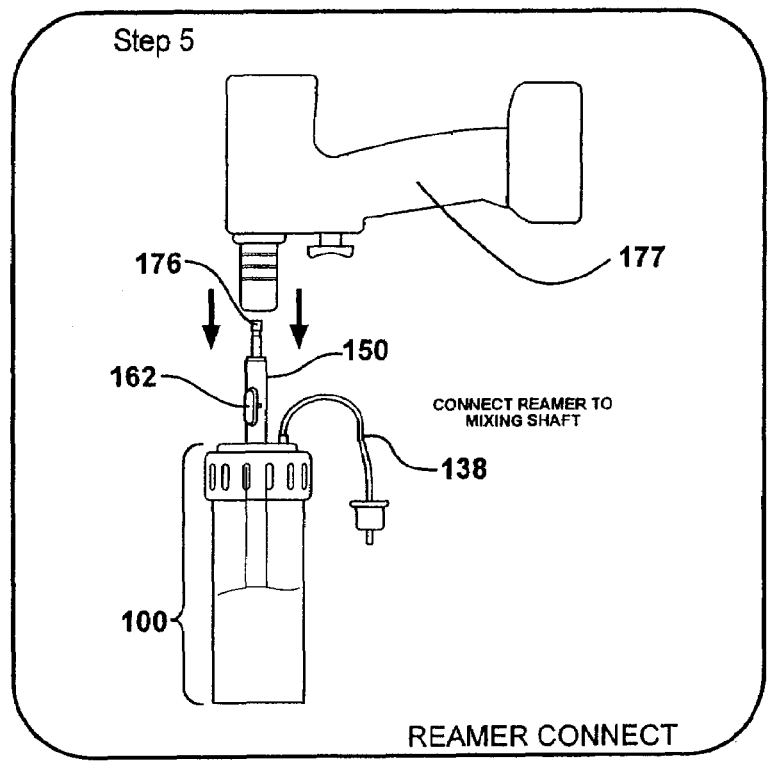

In STEP 5, shown in FIG. 37, with the vacuum drawn, the power tool (reamer) is then connected to the mixing shaft 150.

Figure 38:
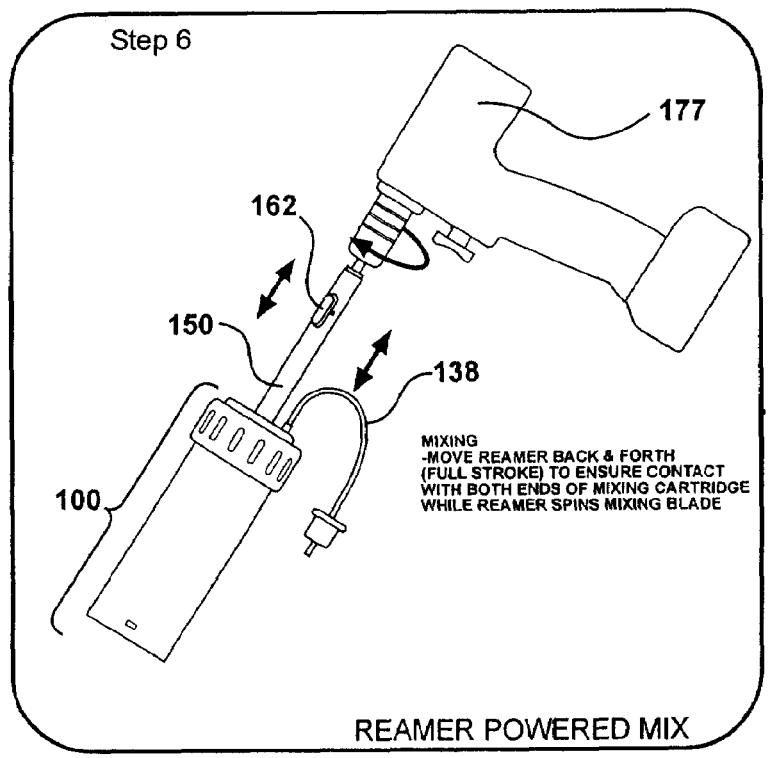

In STEP 6, shown in FIG. 38, with the vacuum still drawn, the mixing shaft 150 is moved axially with respect to the mixing cartridge 100 and rotated by the power tool. The blade 152 (not shown in FIG. 38) is moved axially the entire extent of the mixing cartridge 100 while rotating to ensure that the liquid and powder components are fully mixed.

Figure 39:
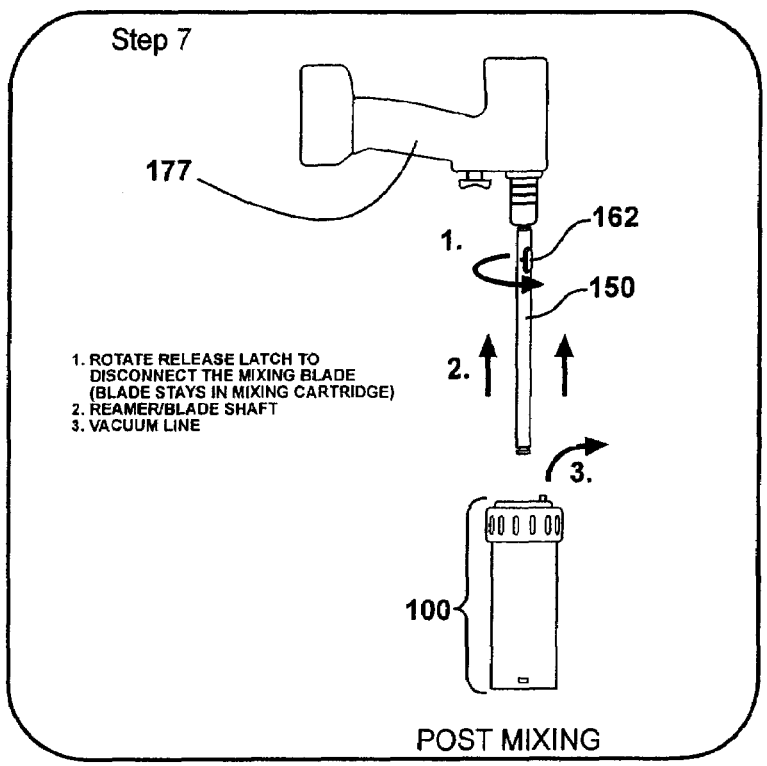

In STEP 7, shown in FIG. 39, once mixed, the release latch 162 is moved to release the blade 152 (not shown in FIG. 39). The blade 152 remains in the mixing chamber 108 once released. The mixing shaft 150 is then removed from the mixing cartridge 100. Mixing is now complete.

Figure 40:
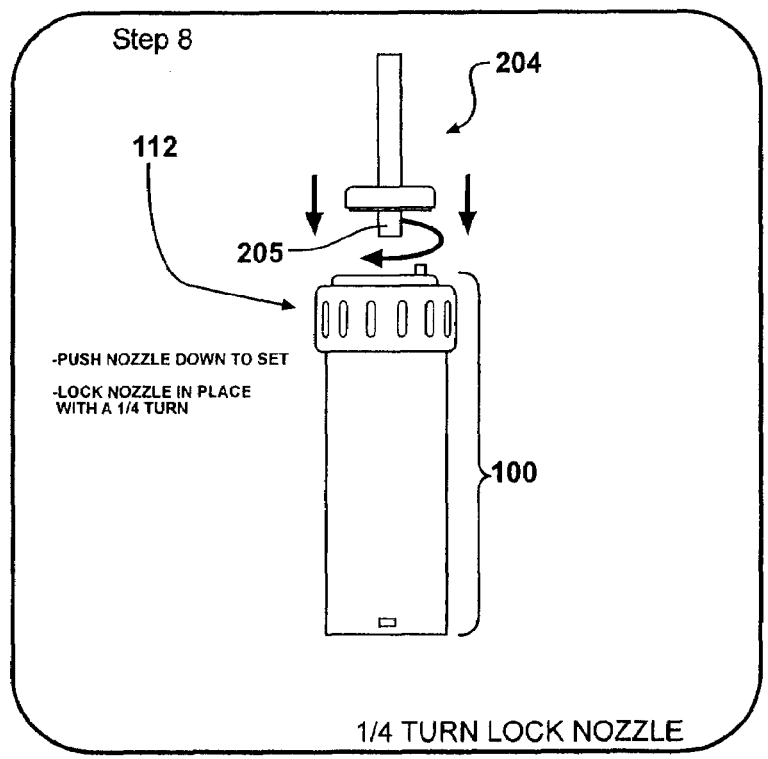

In STEP 8, shown in FIG. 40, the nozzle 204 is pushed down on the cap 112 and rotated into place.

Figure 41:
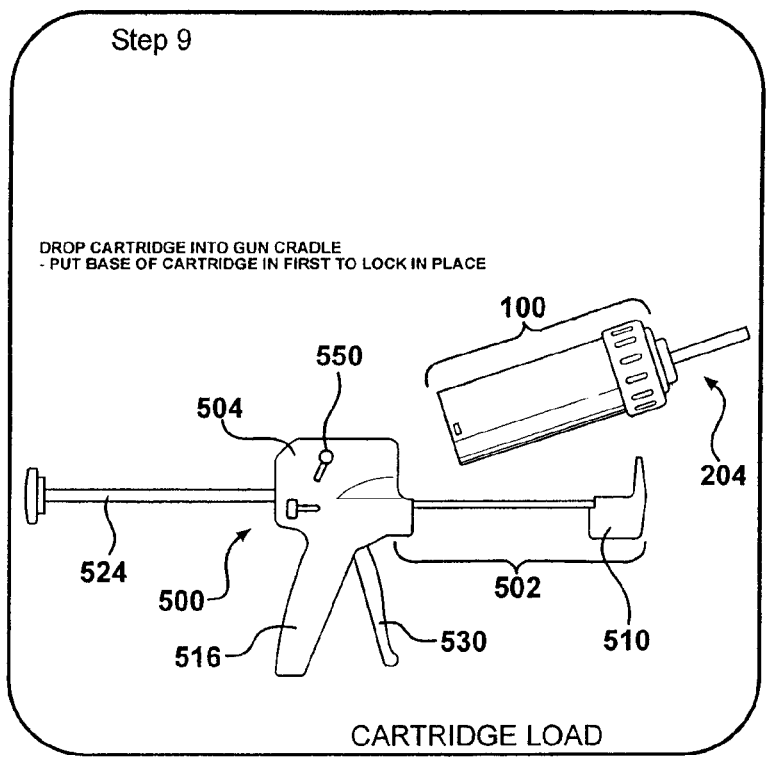

In STEP 9, shown in FIG. 41, the mixing cartridge 100 is positioned in the cradle 502.

Figure 42:
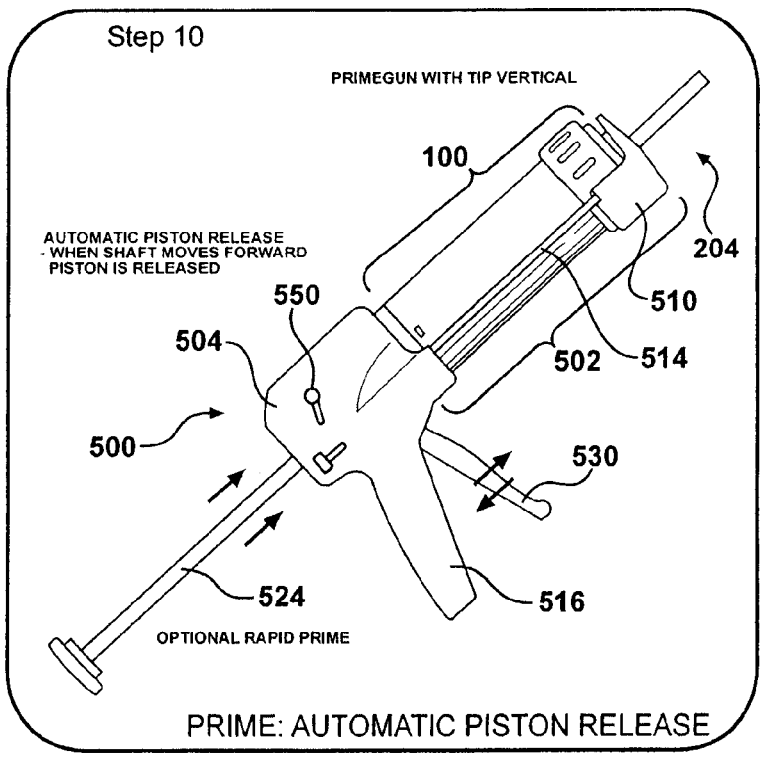

In STEP, shown in FIG. 42, the piston 114 is released from the distal end 106 of the cylinder 102 and the delivery gun 500 is primed and ready to discharge the bone cement from the mixing cartridge 100.

It will be appreciated that the above description relates to the disclosed embodiments by way of example only. Many apparent variations of the disclosed invention will be known to those of skill in this area and are considered to be within the scope of this invention and are considered to be within the scope of the following claims. Obviously, many modifications and variations of the present invention are possible in light of the above teachings.

What is claimed is:

1. A bone cement mixing and delivery system for mixing components of bone cement to form a bone cement mixture and delivering the bone cement mixture to a target site, said system comprising:
   a cartridge having proximal and distal ends, said cartridge comprising;
      a wall extending between said ends,
      a piston releasably secured to said wall in a locked position near said distal end, and
      a locking member for releasably securing said piston in said locked position near said distal end,
   a delivery device adapted to hold said cartridge, said delivery device comprising;
      a casing, and
      a drive mechanism supported by said casing and advanceable relative to said casing to discharge the bone cement mixture from said cartridge wherein said drive mechanism includes a release mechanism for engaging said locking member to unlock said piston.

2. A bone cement mixing and delivery system as set forth in claim 1 wherein said wall is disposed about a longitudinal axis and defines at least one slot, said locking member including at least one locking tab protruding into said at least one slot in said locked position.

3. A bone cement mixing and delivery system as set forth in claim 2 wherein said at least one slot is further defined as a plurality of slots and said at least one locking tab is further defined as a plurality of locking tabs protruding into said slots in said locked position.

4. A bone cement mixing and delivery system as set forth in claim 3 wherein said locking member includes a resilient portion biasing said plurality of locking tabs into said slots.

5. A bone cement mixing and delivery system as set forth in claim 4 wherein said plurality of slots include a pair of diametrically opposed slots and said plurality of locking tabs include a pair of diametrically opposed locking tabs protruding radially outwardly into said diametrically opposed slots under the bias of said resilient portion.

6. A bone cement mixing and delivery system as set forth in claim 5 wherein said resilient portion extends between said diametrically opposed locking tabs to bias said diametrically opposed locking tabs radially outwardly into said diametrically opposed slots.

7. A bone cement mixing and delivery system as set forth in claim 6 wherein said resilient portion is integral with said diametrically opposed locking tabs and extends in a thin resilient ribbon portion between said diametrically opposed locking tabs.

8. A bone cement mixing and delivery system as set forth in claim 3 wherein said piston defines a pair of carrier slots for slidably retaining said plurality of locking tabs.

9. A bone cement mixing and delivery system as set forth in claim 3 wherein said locking member includes a plurality of release portions and said release mechanism engages said plurality of release portions to move said plurality of release portions and unlock said piston.

10. A bone cement mixing and delivery system as set forth in claim 9 wherein said plurality of release portions are further defined as a plurality of fingers engageable by said release mechanism to urge said plurality of locking tabs radially inwardly and withdraw said plurality of locking tabs from said plurality of slots in said wall to unlock said piston.

11. A bone cement mixing and delivery system as set forth in claim 2 wherein said locking member includes at least one release portion and said release mechanism engages said at least one release portion to move said at least one release portion and unlock said piston.

12. A bone cement mixing and delivery system as set forth in claim 11 wherein said at least one release portion includes a cam surface engageable by said release mechanism to slide said at least one release portion radially inwardly and withdraw said at least one locking tab from said at least one slot thereby unlocking said piston.

* * * * *